United States Patent [19]

Lipsky et al.

[11] Patent Number: 5,668,112
[45] Date of Patent: *Sep. 16, 1997

[54] HYDROPHOBIC PEPTIDE ESTERS AND AMIDES

[75] Inventors: Peter E. Lipsky, Dallas; Dwain L. Thiele, Coppell, both of Tex.

[73] Assignee: Board of Regents, The University of Texas Sys., Austin, Tex.

[*] Notice: The term of this patent shall not extend beyond the expiration date of Pat. No. 4,752,602.

[21] Appl. No.: 310,677

[22] Filed: Sep. 22, 1994

Related U.S. Application Data

[60] Continuation of Ser. No. 123,430, Sep. 17, 1993, abandoned, which is a division of Ser. No. 684,010, Apr. 11, 1991, Pat. No. 5,304,474, which is a continuation of Ser. No. 324,151, Mar. 15, 1989, Pat. No. 5,068,223, which is a continuation-in-part of Ser. No. 168,177, Mar. 15, 1988, Pat. No. 5,047,041, which is a continuation-in-part of Ser. No. 774,051, Sep. 9, 1985, Pat. No. 4,752,602.

[51] Int. Cl.$^6$ ............................................. A61K 38/05
[52] U.S. Cl. ........................... 514/19; 562/575; 562/445; 562/444; 548/496
[58] Field of Search ...................... 514/19, 18; 530/331; 562/575, 445, 444; 548/496

[56] References Cited

U.S. PATENT DOCUMENTS

| 4,752,602 | 6/1988 | Lipsky | 514/19 |
| 5,047,401 | 9/1991 | Lipsky | 514/19 |
| 5,068,223 | 11/1991 | Lipsky | 514/19 |
| 5,304,474 | 4/1994 | Lipsky | 435/101 |

OTHER PUBLICATIONS

Thiele Proc Natl Acad Sci, 82, 2468, 1985.
Metrione Biochem 14, 5249, 1975.
McDonald (J Biol Chem 244 6199, '69).

*Primary Examiner*—Cecilia J. Tsang
*Assistant Examiner*—David Lukton
*Attorney, Agent, or Firm*—Denise L. Mayfield

[57] ABSTRACT

Esters or amides of a peptide, preferably a dipeptide, consisting essentially of natural or synthetic L-amino acids with hydrophobic side chains were found to have specific cellular toxicities. Preferable amino acids of the peptide are leucine, phenylalanine valine, isoleucine, alanine, proline, glycine or aspartic acid beta methyl ester. Preferable dipeptides are L leucyl L-leucine, L-leucyl L-phenylalanine, L-valyl L-phenylalanine, L-leucyl L-isoleucine, L-phenylalanyl L-phenylalanine, L-valyl L-leucine, L-leucyl L-alanine, L-valyl L-valine, L-phenylalanyl L leucine, L prolyl L-leucine, L-leucyl L-valine, L-phenylalanyl L-valine, L glycyl L-leucine, L-leucyl L-glycine, glycyl L-phenylalanine and L-aspartyl beta methyl ester L-phenylalanine. Most preferable dipeptides are L-leucyl L-leucine, L-leucyl L-phenylalanine, L-valyl L-phenylalanine, L-phenylalanyl L-leucine, L-leucyl L-isoleucine L-phenylalanyl L-phenylalanine and L-valyl L-leucine.

The ester or amide of the dipeptide is most preferably alkyl, aralkyl or aryl a preferred alkylester is a methyl ester and may also be an ethyl ester or alkyl of up to about four carbon atoms such as propyl, isopropyl, butyl or isobutyl. Yet larger alkyl substituents may also be functional judging from the beta naphthyl substituent which is functional in certain embodiments.

These alkyl, aryl or arylkyl esters and amides of dipeptides consist essentially of amino acids with hydrophobic side chains may be used to deplete cytotoxic T-lymphocytes or natural killer cells from organisms, cell populations or tissues.

6 Claims, 11 Drawing Sheets

HYDROPHOBIC PEPTIDE ESTERS AND AMIDES

This is a continuation of application Ser. No. 08/123,430, filed Sep. 17, 1993, now abandoned, which is a divisional of application Ser. No. 07/684,010, filed Apr. 11, 1991, now U.S. Pat. No. 5,304,474. U.S. Pat. No. 5,304,474 is a continuation of application Ser. No. 07/324,151, filed Mar. 15, 1989, now U.S. Pat. No. 5,068,223. U.S. Pat. No. 5,068,223 is a C.I.P of application Ser. No. 07/168,177, filed Mar. 15, 1988, now U.S. Pat. No. 5,047,401. U.S. Pat. No. 5,047,401 is a C.I.P of application Ser. No. 06/774,051, filed Sep. 9, 1985, now U.S. Pat. No. 4,752,602.

BACKGROUND OF THE INVENTION

The present invention concerns certain peptide esters and their uses, for example, in the ablation of certain cell-mediated immune responses. For brevity and clarity, many of the terms used herein have been abbreviated and these abbreviations include those shown in Table 1. Research involved in the development of the invention was supported by grants from the United States government.

L-leucine methyl ester (Leu-OMe) has previously been used as a lysosomotropic agent (Thiele et al. (1983) J. Immunol. V 131, pp 2282–2290; Goldman et al. (1973) J. Biol. Chem. V 254, p 8914). The generally accepted lysosomotropic mechanism involved leu-OMe diffusion into cells and into lysosomes, followed by intralysosomal hydrolysis to leucine and methanol. The more highly ionically charged leucine, largely unable to diffuse out of the lysosome, caused osmotic lysosomal swelling and rupture. The fate of leu-OMe subjected to rat liver lysosomes was additionally suggested by Goldman et al. (1973) to involve a transpeptidation reaction and a resultant species—"presumably the dipeptide" which was "further hydrolyzed to free amino acids". A subsequent and related paper by Goldman (FEBS (Fed. Europ. Biol. Sci.) Letters V 33, pp 208–212 (1973)) affirmed that non-methylated dipeptides were thought to be formed by lysosomes.

L-amino acid methyl esters have been specifically shown to cause rat liver lysosomal amino acid increases (Reeves (1979) J. Biol. Chem. V 254, pp 8914–8922). Leucine methyl ester has been shown to cause rat heart lysosomal swelling and loss of integrity (Reeves et al., (1981) Proc. Nat'l. Acad. Sci., V 78, pp 4426–4429).

TABLE 1

| Substance | Abbreviations Symbol |
|---|---|
| L-leucine | leu or L |
| L-phenylalanine | phe or P |
| L-alanine | ala or Al |
| L-glycine | gly or G |
| L-serine | ser or S |
| L-tyrosine | tyr or T |
| L-arginine | arg or Ar |
| L-lysine | lys or Ly |
| L-valine | val or V |
| L-isoleucine | ile or I |
| L-proline | pro or P |
| L-glutamic acid | glu or G |
| L-aspartic acid | asp or As |
| L amino acid methyl esters | e.g. Leu—OMe |
| L amino acid ethyl esters | e.g. Leu—OEt |
| L amino acid benzyl esters | e.g. Leu—OBz |
| D-amino acids | e.g. D—Leu |

TABLE 1-continued

| | |
|---|---|
| D-amino acids methyl esters | e.g. D—Leu—OMe |
| dipeptides of L-amino acids | e.g. Leu—Leu |
| methyl esters of dipeptide | e.g. Leu—Leu—OMe or LLOMe |
| L amino acids | |
| dipeptide amides | e.g. L—Leu—L—Leu—NH$_2$ |
| dipeptidyl peptidase-I | DPPI |

| cell fraction or type | Symbol |
|---|---|
| mononuclear phagocytes | MP |
| polymorphonuclear leucocytes | PMN |
| natural killer cells | NK |
| peripheral blood lymphocytes | PBL |
| peripheral blood mononuclear cells | PBM |
| cytotoxic T-lymphocytes | CTL |
| glass or nylon wool adherent cells | AC |
| glass or nylon wool non-adherent cells | NAC |

Other Materials

| | |
|---|---|
| phosphate buffered saline | PBS |
| thin layer chromatography | TLC |
| fluorescence activated cell sorter | FACS |
| mixed lymphocyte culture | MLC |

Miscellaneous

| | |
|---|---|
| effector:target cell ratio | E:T |
| fetal bovine serum | FBS |
| University of Texas Health Science Center, Dallas, Texas. | UTHSCD |
| Standard error of mean | SEM |
| probability of significant difference (Student's t-test) | P |
| Graft versus host disease | GVHD |
| Maximum velocity | Vmax |
| Micromolar | micro-M |
| Level at which there is a 50% loss of cell function | LD$_{50}$ |
| Trichloracetic acid | TCA |
| Phenylmethylsulfonyl fluoride | PMSF |
| Glycylphenylalanine diazomethane | Gly—Phe—CHN$_2$ |
| Mean survival time | MST |

Natural killer cells are large granular lymphocytes that spontaneously lyse tumor cells and virally-infected cells in the absence of any known sensitization. This cytotoxic activity can be modulated by a host of pharmacologic agents that appear to act directly on NK effector cells. NK activity has been shown to be augmented after exposure to interferons (Gidlund et al., Nature V 223, p 259), interleukin 2, (Dempsey, et al. (1982) J. Immunol. V 129, p 1314) (Domzig, et al. (1983) J. Immunol. V 130, p 1970), and interleukin 1 (Dempsey et al. (1982) J. Immunol. V 129, p 1314), whereas target cell binding is inhibited by cytochalasin B, (Quan, et al. (1982) J. Immunol. V 128, p 1786), dimethyl sulfoxide, 2-mercaptoethanol, and magnesium deficiency (Hiserodt, et al. (1982) J. Immunol. V 129, p 2266). Subsequent steps in the lytic process are inhibited by calcium deficiency (Quan et al. (1982) J. Immunol. V 128, p 1786, Hiserodt, et al. (1982) J. Immunol. V 129, p 2266), lysosomotropic agents (Verhoef, et al. (1983) J. Immunol. V 131, p 125), prostaglandin E$_2$ (PGE$_2$ (Roder, et al. (1979) J. Immunol. V 123, p 2785, Kendall, et al. (1980) J. Immunol. V 125, p 2770), cyclic AMP (Roder, et al. (1979) J. Immunol. V 123, p 2785, Katz (1982) J. Immunol. V 129, p 287), lipomodulin (Hattori, et al. (1983) J. Immunol. V 131, p 662), and by antagonists of lipoxygenase (Seaman (1983) J. Immunol V 131 p 2953). Furthermore, it has been demonstrated that PGE$_2$ and reactive metabolites of oxygen produced by monocytes (MP) or polymorphonuclear leukocytes (PMN) can inhibit NK cell function (Koren, et al. (1982) Mol. Immunol. V 19, p 1341; and Seaman, et al. (1982) J. Clin. Invest. V 69, p 876).

Previous work by the present applicants has examined the effect of L-leucine methyl ester on the structure and function of human peripheral blood mononuclear cells (PBM) (Thiele, et al. (1983) J. Immunol. V 131, p 2282.

Human peripheral blood mononuclear cells (PBM) are capable of mediating a variety of cell-mediated cytotoxic functions. In the absence of any known sensitization, spontaneous lysis of tumor cells and virally-infected cells is mediated by natural killer cells (NK) contained within the large granular lymphocyte fraction of human PBM Timonen et al. (1981) v. J. Exp Med. V 153 pp 569–582. After lymphokine activation, additional cytotoxic lymphocytes capable of lysing a broad spectrum of tumor cell targets can be generated in in vitro cultures (Seeley et al. (1979) J. Immunol. V 123, p 1303; and Grimm et al. (1982) J. Exp. Med. V 155, p 1823). Furthermore, lymphokine activated peripheral blood mononuclear phagocytes (MP) are also capable of lysing certain tumor targets (Kleinerman et al. (1984) J. Immunol. V 133, p 4). Following antigen-specific stimulation, cell-mediated lympholysis can be mediated by cytotoxic T lymphocytes (CTL).

While a variety of functional and phenotypic characteristics can be used to distinguish these various types of cytotoxic effector cells, a number of surface antigens and functional characteristics are shared. Thus, the antigens identified by the monoclonal antibodies OKT8 (Ortaldo et al. (1981) J. Immunol. V 127, p 2401; and Perussia et al. (1983) J. Immunol. V 130, p 2133), and OKT11 (Perussia et al. (1983) J. Immunol. V 130, p 2133; and Zarling et al. (1981) J. Immunol. V 127, p 2575) are found on both CTL and NK while the antigen identified by OKM1 is shared by MP and NK (Zarling et al. (1981) J. Immunol. V 127, p 2575; Ortaldo et al. (1981) J. Immunol. V 127, p 2401; Perussia et al. (1983) J. Immunol. V 130, p 2133; and Breard et al. (1980) J. Immunol. V 124, p 1943. Furthermore, cytolytic activity of both NK and MP is augmented by interferons, (Kleinerman et al. (1984) J. Immunol. V 133, p 4; Gidlund et al. (1978) Nature V 223, p 259; and Trinchieri et al. (1978) J. Exp. Med. V 147, p 1314). Finally, use of metabolic inhibitors has demonstrated some parallels in the lytic mechanism employed by CTL and NK (Quan et al. (1982) J. Immunol. V 128, p 1786; Hiserodt et al. (1982) J. Immunol. V 129, p 1782; Bonavida et al. (1983) Immunol. Rev. V 72, p 119; Podack et al. (1983) Nature V 302, p 442; Dennert et al. (1983) J. Exp. Med. V 157, p 1483; and Burns et al. (1983) Proc. Nat'l. Acad. Sci. V 80, p 7606).

SUMMARY OF THE INVENTION

A peptide, amide or ester consisting essentially of natural or synthetic L-amino acids with hydrophobic side chains may be used to deactivate natural killer cells (NK). Preferable amino acids of such peptides are leucine, phenylalanine, valine, isoleucine, alanine, proline, glycine or aspartic acid beta methyl ester. Preferable dipeptides are L leucyl L-leucine, L-leucyl L-phenylalanine, L-valyl L-phenylalanine, L-leucyl L-isoleucine, L-phenylalanyl L-phenylalanine, L-valyl L-leucine, L-leucyl L-alanine, L-valyl L-valine, L-phenylalanyl L-leucine, L-prolyl L-leucine, L-leucyl L-valine, L-phenylalanyl L-valine, L glycyl L-leucine, L-leucyl L-glycine or L-aspartyl beta methyl ester L-phenylalanine. The most preferable dipeptides are glycyl L-phenylalanine, L-leucyl L-leucine, L-leucyl L-phenylalanine, L-valyl L-phenylalanine, L-phenylalanyl L-leucine, L-leucyl L-isoleucine, L-phenylalanyl L-phenylalanine and L-valyl L-leucine.

The amide or ester of the peptide is preferably a benzyl, methyl ethyl or alkyl of up to about four carbon atoms such as propyl, isopropyl, butyl or isobutyl. Larger alkyl groups may be used. Aralkyl or aryl derivatives, for example benzyl and napthyl may be particularly effective.

The present invention further involves a method for deactivating natural killer cells or cytotoxic T-lymphocytes comprising the step of treating said cells with an aqueous solution comprising a biologically effective level of a dipeptide in ester or substituted amide form consisting essentially of natural or synthetic L-amino acids with hydrophobic side chains, said ester form being an aryl, alkaryl or aralkyl ester and said amide form being a substituted amide. This aqueous solution more preferably comprises a biologically effective level of a dipeptide in ester or substituted amide form, said dipeptide consisting essentially of at least one of L-leucine, L-phenylalanine, L-valine, L-isoleucine, L-alanine, L-proline, glycine, and L-aspartic acid beta methyl ester, said ester form being an aryl, alkaryl or aralkyl ester and said amide form being a substituted amide. The cells being deactivated may be in vitro or may be yet within an animal. In the latter case the animal is parenterally administered a biologically effective amount of the dipeptide in ester or substituted amide form.

Preferably, the dipeptide in ester or substituted amide form has the following structure:

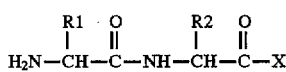

wherein

R1 and R2 represent hydrophobic side chains of amino acids;

X represents —OR3 or —NHR4;

R3 is selected from the group consisting of aryl, aralkyl, and alkaryl; and

R4 is selected from the group consisting of alkyl, aryl, aralkyl and alkaryl.

This deactivation of natural killer cells and cytotoxic T-lymphocytes may also be adapted as a method for inhibiting bone marrow graft versus host disease comprising the step of contacting the bone marrow cells to be grafted with an aqueous solution comprising a biologically effective level of a dipeptide in ester or substituted amide form consisting essentially of natural or synthetic L-amino acids with hydrophobic side chains, said ester form being an aryl, alkaryl or aralkyl ester and said amide form being a substituted amide. This aqueous solution again more preferably comprises a biologically effective level of a dipeptide in ester or substituted amide form, said dipeptide consisting essentially of at least one of L-leucine, L-phenylalanine, L-valine, L-isoleucine, L-alanine, L-proline, glycine, and L-aspartic acid beta methyl ester, said ester form being an aryl, alkaryl or aralkyl ester and said amide form being a substituted amide. For in vitro deactivation of natural killer cells or cytotoxic T-lymphocytes, the biologically effective level should be between about 1 micromolar and about 250 micromolar, depending upon the particular agent being used and its effectiveness.

Graft vs. host disease (GVHD) remains one of the main problems associated with bone marrow transplantation. The current studies were undertaken to determine whether treatment of the donor inoculum with the anticytotoxic cell compound L-leucyl-L-leucine methyl ester (Leu-Leu-OMe) would alter the development of GVHD in a murine model. Irradiated recipient mice transplanted with a mixture of control bone marrow and spleen cells from naive semiallogeneic donors died rapidly from GVHD, whereas the recipients of cells incubated with 250 micro-M Leu-Leu-OMe all survived. In addition, Leu-Leu-OMe treatment of cells obtained from donors immunized against host alloantigens resulted in significantly prolonged survival. Phenotypic characterization of spleen cells from the various groups of mice that had received Leu-Leu-OMe-treated cells and survived consistently revealed the donor phenotype. Treatment of marrow cells with 250 micro-M Leu-Leu-OMe appeared to have no adverse effects on stem cell function. Erythropoiesis was undiminished, as assayed by splenic 5-iodo-2'-deoxyuridine-$^{125}$I uptake. Moreover, granulocytic and megakaryocytic regeneration were histologically equivalent in the spleens of recipients of control or Leu-Leu-OMe-treated cells. Treatment of the donor inoculum with Leu-Leu-OMe thus prevents GVHD in this murine strain combination with no apparent stem cell toxicity.

In clinical application, the present invention additionally involves a method of inhibiting the rejection of tissue transplanted into a host. This method comprises the steps of identifying a prospective transplant recipient; and treating the prospective recipient with an aqueous solution comprising a biologically effective level of a dipeptide in ester or substituted amide form consisting essentially of natural or synthetic L-amino acids with hydrophobic side chains, said ester form being an aryl, alkaryl or aralkyl ester and said amide form being a substituted amide. This aqueous solution also more preferably comprises a biologically effective level of a dipeptide in ester or substituted amide form, said dipeptide consisting essentially of at least one of L-leucine, L-phenylalanine, L-valine, L-isoleucine, L-alanine, L-proline, glycine, and L-aspartic acid beta methyl ester, said ester form being an aryl, alkaryl or aralkyl ester and said amide form being a substituted amide.

A similar clinical method for treating a patient with aplastic anemia is further a component of the present invention, the method differing primarily in comprising the initial step of identifying a patient with aplastic anemia.

Likewise, the above procedure may be used for treating a patient having a tumor sensitive to treatment with hydrophobic dipeptide esters or amides, this method differing primarily in that it first involves the step of identifying a patient with such a tumor. Such tumors characteristically are cells similar to natural killer cells or cytotoxic T-lymphocytes.

A patient with an autoimmune disease, thought to be mediated by natural killer cells and/or cytotoxic T-lymphocytes may also be treated by the methods of the present invention. The method would initially comprise the step of identifying a patient with autoimmune disease and would thereafter be similar to that described for the other clinical disorders.

For clinical treatments involving parenteral administration of the compounds of the present invention, the biologically effective amount administered is between about 10 mg/kg body weight and 300 mg/kg body weight; preferably about $1 \times 10^{-4}$ moles/kg body weight. The aqueous solutions of the present invention include any of those suitable for in vivo administration free of toxins and preferably being of an approximate physiological pH and osmolality.

Preferred substituted dipeptide amides of the present invention include those having an alkyl, aryl, aralkyl or alkaryl-substituent. A preferred substituted amide form has an aryl substituent, most preferably beta napthyl. A particularly preferred specific dipeptide substituted amide usable in the practice of the present invention is glycyl L-phenylalanyl beta napthylamide.

Preferred dipeptide esters of the present invention include those formed with an alkaryl alcohol, most preferably benzyl alcohol. The term "alkaryl" is used herein to indicate an alkyl group bound in amide or ester linkage to the dipeptide and having an aryl group bound thereto. A particularly preferred dipeptide ester of the present invention is L-leucyl-L-leucyl benzyl ester. The term "aralkyl" is used herein to indicate an aryl group bound in amide or ester linkage to a dipeptide of the present invention and having an alkyl group bound thereto. It is understood that those skilled in the art may make many variations in group substitutions on the alkyl, aryl, aralkyl and alkaryl groups substituents of the present invention and still be within the presently claimed invention.

Preferred dipeptides of the present invention include L-leucyl L-leucine, L-leucyl L-phenylalanine, L-valyl L-phenylalanine, L-phenylalanyl L-leucine, L-leucyl L-isoleucine, L-phenylalanyl L-phenylalanine, L-valyl L-leucine, L-leucyl L-alanine, L-valyl L-valine, L-prolyl L-leucine, L-leucyl L-valine, L-phenylalanyl L-valine, glycyl L-leucine, L-leucyl glycine, and L-aspartyl beta methyl ester L-phenylalanine. A more preferred group of dipeptides is L-leucyl L-leucine, L-leucyl L-phenylalanine, L-valyl L-phenylalanine, glycyl L-phenylalanine, L-phenylalanyl L-leucine, L-leucyl L-isoleucine, L-phenylalanyl L-phenylalanine and L-valyl L-leucine.

The present invention describes a general method for deactivating natural killer cells or cytotoxic T-lymphocytes. This general method comprises the step of treating said cells with an aqueous solution comprising a biologically effective level of a compound which competitively inhibits lymphocyte uptake of Leu-Leu-OMe and is polymerized by dipeptidyl peptidase I to form a membranolytic product. This more general method may be applied as a method of inhibiting the rejection of tissue transplanted into a host. In this application the method comprises the steps of identifying a prospective transplant recipient and treating the prospective recipient with a compound which competitively inhibits lymphocyte uptake of Leu-Leu-OMe and is polymerized by dipeptidyl peptidase I to form a membranolytic product.

Patients with aplastic anemia may be likewise treated by initially identifying a patient with aplastic anemia and then treating the patient with a compound which competitively inhibits lymphocyte uptake of Leu-Leu-OMe and is polymerized by dipeptidyl peptidase I to form a membranolytic product.

This more general method may also be used to treat a patient with an autoimmune disease. The method then comprises the steps of identifying a patient with autoimmune disease and then treating the patient with a compound which competitively inhibits lymphocyte uptake of Leu-Leu-OMe and is polymerized by dipeptidyl peptidase I to form a membranolytic product.

The present invention also includes a method for treating a patient having a tumor which is rich in dipeptidyl peptidase I (i.e., at least about 0.3 nM napthylamine/hr/ug protein). The method comprises the steps of identifying a patient with such a tumor, and treating the patient with a compound which competitively inhibits lymphocyte uptake of Leu-Leu-OMe and is polymerized by dipeptidyl peptidase I to form a membranolytic product.

An analogous method for inhibiting bone marrow graft versus host disease may also be so generalized. Such a method comprises the step of contacting bone marrow cells to be grafted with an aqueous solution comprising a biologically effective level of a compound which competitively inhibits lymphocyte uptake of Leu-Leu-OMe and is polymerized by dipeptidyl peptidase I to form a membranolytic product.

DETAILED DESCRIPTION OF PREFERRED EMBODIMENTS

Figure 1:
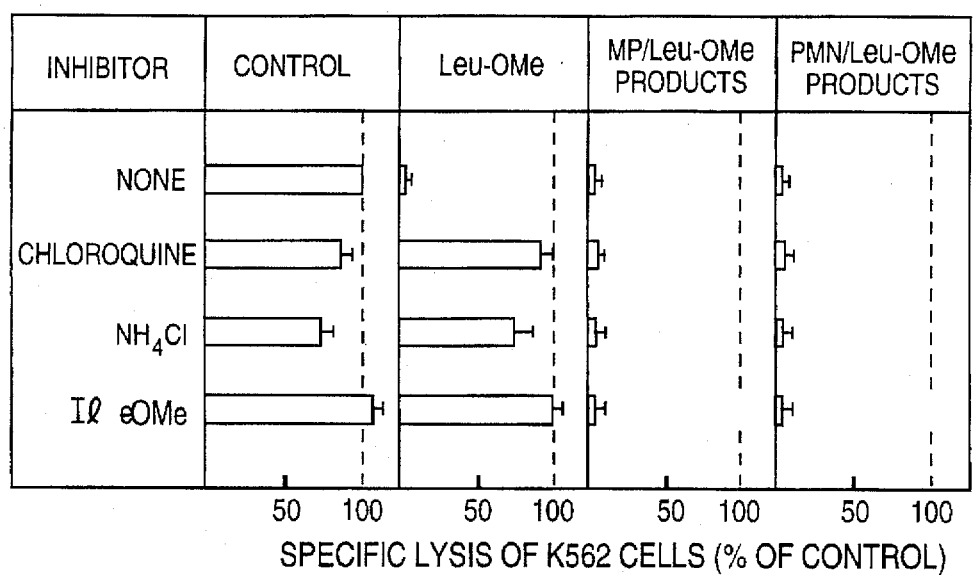
FIG. 1 shows that whereas ablation of NK function during incubation with Leu-OMe can be blocked by lysosomotropic agents, there is a product formed during incubation of Leu-OMe with MP or PMN which has effects on NK function no longer blocked by lysosomal inhibitors.

The present invention concerns new compounds and their uses in ablating particular cell types and their functions. The presently described invention relates to the discovery that peptide esters and amides may be cytotoxic to particular cell types.

It has further been found that alkyl aralkyl and aryl esters or amides of peptides consisting essentially of natural or synthetic amino acids with hydrophobic side chains may function cytotoxically to deactivate natural killer cells (NK) and cytotoxic T lymphocytes (CTL). By the term "hydrophobic" as used herein, is meant uncharged in aqueous solution at physiological pH and also as having no hydroxyl, carboxyl or primary amino groups.

Treatment of NK or CTL with an effective level of a peptide amide or ester consisting essentially of natural or synthetic amino acids with hydrophobic side chains serves to deactivate the cytotoxic functions of said cells. An effective level varies from circumstance to circumstance but generally lies between about 25 micromolar and about 250 micromolar. An effective level for a whole animal dose generally lies between about 100 mg/kg and about 300 mg/kg.

Both methyl ethyl and benzyl esters or amides of peptides consisting essentially of natural or synthetic amino acids having hydrophobic side chains have been specifically found to deactivate natural killer cells (NK) or cytotoxic T lymphocytes (CTL) and other alkyl esters of these peptides are confidently predicted to have similar or superior effects.

Deactivation of NK or CTL cells with such peptide esters or amides should increase the success of allogeneic bone marrow transplants by lowering the incidence of graft-versus-host disease (GVHD) and thus lessening the incidence of transplant rejection.

Graft versus host disease (GVHD) is a major problem in allogeneic bone marrow transplantation. It occurs in approximately 70% of transplant recipients and causes death in 20% of those (Wells, et al. p 493 in Basic and Clinical Immunology. Fundenbergo et al. (editors) 2nd ed. Lange, (1978)). The disease occurs when cells of the graft (donor) attack the host tissue, causing abnormalities in the immune system and gastrointestinal tract, as well as skin rashes and liver dysfunction. Although T lymphocytes have traditionally been considered to be the primary effector cells in GVHD, recent studies have shown a correlation between the occurrence of the disease and the appearance of NK activity soon after transplantation. These results implicate the donor's NK cells in the etiology of GVHD. Moreover, other studies demonstrate that high levels of NK activity in a bone marrow recipient prior to transplantation are associated with GVHD (Dokhelar et al. (1981) Transplantation V 31 p 61; Lopez et al. (1979) Lancet V 2 p 1103; and Lopez et al. (1980) Lancet V 2 p 1025). Thus, it is theorized that both host and donor NK cells contribute to the development of the disease.

Current regimens for the prevention and treatment of GVHD consist of depleting T-lymphocytes from the donor marrow prior to transplantation and giving the recipient immunosuppressive drugs such as cyclophosphamide and methotrexate, both before and after transplantation. The effectiveness of these regimens might be enhanced by treating donor bone marrow and transplant recipients with dipeptide methyl esters. Potential problems with these procedures include possible non-specific toxicity of therapeutic dipeptide alkyl esters and the re-emergence of NK activity from precursors not sensitive to therapeutic dipeptide alkyl esters.

Currently, bone marrow transplantation is used as a major mode of therapy in treating aplastic anemia, acute myelogenous leukemia, and a variety of immunodeficiency states.

As mentioned above, a major complication of this therapy is graft-versus-host disease (Sullivan et al., Blood V 57, p 207). Severity of GVHD in man correlates with pretransplant levels of natural killer (NK) activity (Lopez et al., Lancet V 2, p 2101). Thus, by virtue of its ability to diminish NK function in vivo, it is contemplated that Leu-Leu-OBz administration, for example, to bone marrow samples prior to their transplantation will be efficacious in diminishing this complication. An effective level of the peptide esters or amides of the present invention for in vitro deactivation of natural killer cells is between about 10 micromolar and about 250 micromolar.

Furthermore, in both murine and human models, the incidence of GVHD is decreased by in vitro treatment of donor bone marrow with agents that deplete mature T cells (Korngold et al., Exp. Med. V 148, p 1687; Reisner et al., Blood V 61, p 341). Since cytotoxic T cells (CTL) derived from donor bone marrow appear to be the final mediators of GVHD, in vitro treatment of donor bone marrow with an agent which selectively damages cytotoxic T cell precursors is also likely to be of benefit. Since such an in vitro action of amides and esters of the present invention, for example Leu-Leu-OMe has now been demonstrated it was expected that these agents would be of benefit in pre-treating donor bone marrow. An effective level of the esters or amides of the present invention for treatment of bone marrow to be transplanted should be between about 10 micromolar and 250 micromolar for ablation of GVHD-mediating CTL and NK. This prediction of effective GVHD prevention has been further supported by experiments described herein.

A second problem in bone marrow transplantation is the failure of engraftment (the transplant does not "take" or is rejected). This problem occurs in 10–20% of transplants and can be caused by several factors, including improper transplantation technique, extensive invasion of the recipient's bone marrow by tumor cells, and rejection of the transplant. The incidence of bone marrow graft failure is also enhanced by pan-T cell depletion of donor marrow (Mitsuyasu, et al. (1986) Annals of Int. Med. v. 105, p. 20).

The discovery that $F^1$ mice could reject transplants of parental bone marrow first indicated that NK cells might be involved in the engraftment failures (Cudkowicz et al. (1971) J. Exp. Med. V 134, p 83; Cudkowicz et al. (1971) J. Exp. Med. V 134, p 1513; and Kiessling et al. (1977) Eur. J. Immunol. V 7, p 655).

Initially graft rejection was thought to be almost totally dependent on T lymphocytes. However, T cells from an $F^1$ hybrid animal do not normally attack parental tissue. Therefore, it was suggested that NK cells, not T cells, mediated the rejection of the parental bone marrow.

Additional support for this hypothesis was derived from the observation that mice of a strain normally incapable of rejecting bone marrow transplants acquire this ability when they are injected with cloned NK cells. (Warren et al. (1977) Nature V 300, p 655,). As a result of these findings, Herberman et al. ((1981) Science V 214), p 24 have suggested that suppression of NK activity might lower the incidence of transplant rejection. This suppression should be achieved by treating the recipient with the peptide esters or amides of the present invention prior to transplantation.

Other clinical uses for the present peptide amides or esters consisting essentially of amino acids with hydrophobic side chains, are other situations where NK or CTL are involved in the pathogenesis of disease. In organ transplants in general (kidney, heart, liver, pancreas, skin, etc.), it is widely accepted that cytotoxic T cells are likely to be the cell type responsible for graft rejection (Mayer et al., J. Immunol. V 134, p 258). Thus, it is contemplated that the in vivo administration of peptide esters or amides of the present invention will be of benefit in preventing allograft rejection.

It is also contemplated that peptide esters or amides of the present invention may be of benefit in other spontaneously occurring disease states. A variety of diseases have been classified as "autoimmune diseases" because of the widely accepted belief that they are caused by disorders in the immune system which cause immunologic damage to "self". Thus, in a variety of diseases, including primary biliary cirrhosis, systemic lupus erythematosus, rheumatoid arthritis, multiple sclerosis, autoimmune hemolytic anemia, etc., various forms of immunologic damage to selected organs occur. In some of these diseases, such as primary biliary cirrhosis, the histologic abnormalities which occur (in this case in the liver) closely resemble those which occur in GVHD or in rejection of a transplanted liver (Fennel, (1981), Pathol. Annu. V 16 p 289. Thus, it is reasonable that similar mechanisms of cytotoxic lymphocyte damage to liver cells may be occurring, and therefore benefit from therapy with peptide esters or amides of the present invention should also occur in such disease states.

The peptide esters or amides of the present invention should be usable chemotherapeutic agents for patients with natural killer cell tumors (generally leukemias), although very few reports of these tumors are found in the literature (Komiyama et al. (1982) Blood V 60, p 1428 (1982); Itoh et al. (1983) Blood V 61, p 940; Komiyama et al. (1984) Cancer V 54 p 1547.

It is contemplated that the peptide esters and amides of the present invention may also be used to treat patients with aplastic anemia and other types of bone marrow dysfunction. This suggestion is based on three sets of observations in human studies: first, NK cells can kill normal bone marrow cells (Hansson, et al. (1981) Eur. J. Immunol. V 11, p 8); second NK cells inhibit growth of blood cell precursors in vitro (Hansson, et al. (1982) J. Immunol. V 129, p 126; Spitzer et al.: Blood V 63, p 260; Torok-Storb et al. (1982) Nature V 298, p 473; Mangan, et al. Blood V 63, p 260); and third, NK-like cells with the ability to inhibit the formation of red blood cells with the ability to inhibit the formation of red blood cells have been isolated from patients with aplastic anemia (Mangan, et al. (1982) J. Clin. Invest. V 70, p 1148; and Nogasawa et al. (1981) Blood V 57, p 1025). Moreover, recent studies in the mouse indicate that NK cells may function to suppress hemopoiesis in vivo (Holmberg et al. (1984) J. Immunol. V 133, p 2933). However, further investigation is desireable before the connection between NK activity and bone marrow dysfunction is considered conclusive.

Generally, when the peptide esters or amides of the present invention are administered to animals, an effective level is between about $1 \times 10^{-4}$ moles/kg and about $1 \times 10$ moles/kg.

The following Examples are presented to more fully illustrate preferred embodiments of the present invention and are not intended to limit the invention unless otherwise so stated in the accompanying claims.

EXAMPLE 1

Cell Preparations and Assays

PBM were separated from heparinized venous blood of healthy donors by centrifugation over sodium diatrizoate-Ficoll gradients (Isolymph, Gallard-Schlesinger Chemical Mfg. Corp., Carle Place, N.Y.). Monocyte-enriched populations ((MP) were prepared from glass adherent cells and MP-depleted lymphocytes from the nonadherent cells remaining after incubation in glass Petri dishes and passage through nylon wool columns as detailed in Rosenberg et al. (1975) (J. Immunol V 122, pp 926–831). PMN were collected by resuspending peripheral blood cells that penetrated sodium diatrizoate-Ficoll gradients and removing erythrocytes nu dextran sedimentation and hypotonic lysis as previously outlined (Thiele et al. (1985) J. Immunol. V 134, pp 786–793.

All cell exposures to the amino acids, dipeptides or their methyl esters were carried out by suspending cells in Dulbecco's phosphate buffered saline (PBS) and incubating them at room temperature with the reagent at the indicated concentration and time interval. After incubation, the cells were washed twice with Hanks' balanced salt solution and resuspended in medium RPMI 1640 (Inland Laboratories, Fort Worth, Tex.) supplemented with 10% fetal bovine serum (Microbiological Associates, Walkersville, Minn.) for assay of function.

Natural killing against K562 target cells was assessed by a 3 hour $^{51}$Cr release assay and percent specific lysis calculated as previously described (Thiele et al. (1985) J. Immunol. V 134, pp 786–793). Percent of control cytotoxicity was calculated using the formula:

Experimental % specific lysis/Control % specific lysis ×100

EXAMPLE 2

General Procedures for Generation, Purification and Characterization of L-leucine Methyl Ester and Its Metabolites MP or PMN (prepared as in Example 1) at a concentration of $25\times10^6$ per ml were suspended in PBS and incubated with 25 mM Leu-OMe for 20 minutes at 22~C. Cell suspensions were then centrifuged at 1000 g for 10 minutes and the supernatants harvested and freeze-dried at −70~C., 100 millitorr atmospheric pressure. In some experiments, Leu-OMe-treated MP or PMN were sonicated to increase the yield of the reaction product. Samples were then extracted with methanol for application to thin layer chromatography (TLC) plates (200 micromolar×20 cm$^2$, Analtech, Newark, Del.). Following development with chloroform/methanol/acetic acid (19:1:12.5 by volume), 1 cm bands were eluted with methanol, dried under nitrogen, and resuspended in 1 ml PBS. Mass spectra were obtained with a Finnegan Model 4021 automated EI/CI, GC/MS system coupled to an Incos data system. Methane was used as the reagent gas for chemical ionization (CI)mass spectral analysis.

EXAMPLE 3

Lysosomotropic Substances and Formation of NK-toxic Products

The addition of Leu-OMe to human PBM was shown to cause rapid death of MP and NK cells but not T or B lymphocytes (Thiele et al. (1985) J. Immunol. V 134, pp 786–793; Thiele et al. (1983) J. Immunol. V 131, pp 2282–2290). Amino acid methyl esters are known to be lysosomotropic compounds, and in previous studies it was found that the lysosomal inhibitors, chloroquine and NH$_4$Cl, prevented Leu-OMe-induced MP toxicity. To assess whether these agents similarly prevented formation of any NK toxic products, the following experiments were carried out, and the results shown in FIG. 1.

PBM (prepared as in Example 1) were incubated with various potential NK toxic agents in the presence or absence of various lysosomal inhibitors for 40 minutes, washed to remove the inhibitor, incubated for 18 hours to permit recovery from any transient inhibition caused by lysosomotropic agents and then tested for NK activity. As can be seen in FIG. 1, neither chloroquine, NH$_4$Cl, nor Ile-OMe had any substantial permanent effect on NK function. In contrast, 5 mM Leu-OMe ablated all NK activity. This activity of Leu-OMe was largely prevented by chloroquine, NH$_4$Cl, or Ile-OMe. The products generated by MP or PMN, after exposure to Leu-OMe also completely removed all NK activity from PBM. In contrast to the effect noted with Leu-OMe, the lysosomal inhibitors did not protect NK cells from the action of this product(s). Additional experiments indicated that the sonicates of MP or PMN had no effect on NK function in this system whereas the supernatants or sonicates of Leu-OMe treated PMN or MP also depleted NK cells from MP depleted lymphocytes. These results therefore suggest that interaction of Leu-Ome with the lysosomal compartment of MP or PMN produced a product which was directly toxic to NK cells through a mechanism that was no longer dependent on lysosomal processing within the NK cell or an additional cell type.

More particularly, the conditions of the manipulations leading to the results shown in FIG. 1 were as follows:

Inhibitors of lysosomal enzyme function prevent generation of an NK toxic product. PBM ($5\times10^6$/ml) or PMN ($25\times10^6$/ml) preincubated with 25 mM Leu-OMe for 30 minutes were added to cells to be ablated. Cells were incubated with these agents for another 30 minutes at 22° C., then washed and cultured for 18 hours at 37° C. before assay of the ability to lyse K562 cells. Data are expressed as percentage of control cytotoxicity observed with an effector:target ratio of 40:1 (results at other E:T were similar).

EXAMPLE 4

Ablation of NK Function by PMN produced Leu OMe Product

Figure 2:
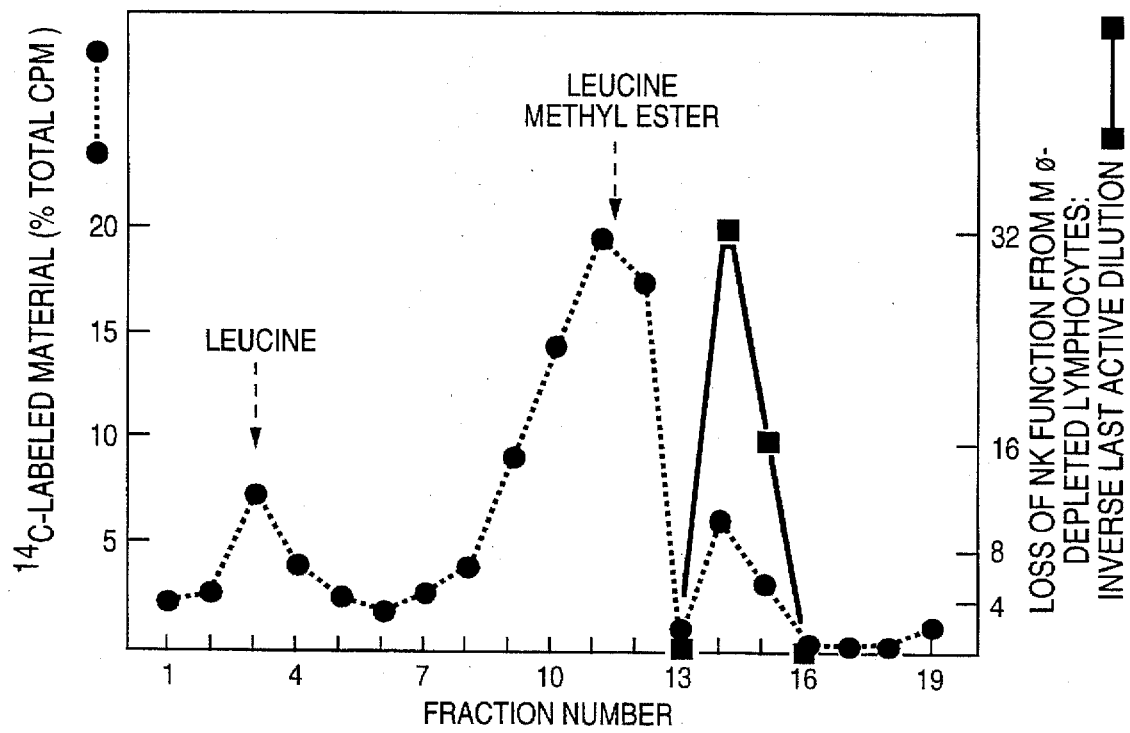
FIG. 2 shows Leu-OMe products of PMN in terms of radioactivity and NK suppressive effects of TLC fractions.

When the NK toxic properties of MP-Leu-OMe, or PMN-Leu-OMe incubation mixtures were evaluated, it was found that this activity was stable in aqueous solutions for more than 48 hours at 4° C., but labile at 100° C., retarded on Sephadex G-10 columns; dialyzable through 1000 MWCO (molecular weight cut-off) membranes, and could be extracted by chloroform-methanol (3:1, by volume). As shown in FIG. 2, when $^{14}$C-leucine methyl ester was incubated with PMN and the supernatants subsequently separated by TLC, three major peaks of $^{14}$C activity were found. One of these peaks corresponded to leucine methyl ester itself and one to free leucine while the third represented a new product. This third peak accounted for about 10% of the total $^{14}$C-labeled material. When MP-depleted lymphocytes were exposed to each TLC fraction, the third peak was found to contain all NK toxic activity. This NK toxic activity not only appeared to be $^{14}$C labeled but was also ninhydrin positive, suggesting that it was a metabolite which still retained an amino group as well as part of the carbon structure of Leu-OMe. An identical $^{14}$C labeled ninhydrin positive product was detected by TLC of MP-Leu-OMe incubation mixture supernatants or sonicates. The production by PMN or MP of this metabolite was inhibited by chloroquine, NH$_4$Cl, or Ile-OMe (data not shown).

Ablation of NK function is mediated by a metabolite of Leu-OMe. PMN ($25\times10^6$/ml) were incubated with 25 mM ¹⁴C-Leu-OMe for 30 minutes and supernatants harvested for TLC analysis. MP-depleted lymphocytes ($2.5\times10^6$ cells/ml) were exposed to varying dilutions of each TLC fraction for 30 minutes, washed and cultured for 2 hours prior to cytotoxicity assay at E:T ratio of 20:1. Samples were considered to contain an NK toxic product when percent specific lysis was less than 25% of control. FIG. 2 shows these results.

EXAMPLE 5

Characterization of the NK-toxic Metabolite

Figure 3A:
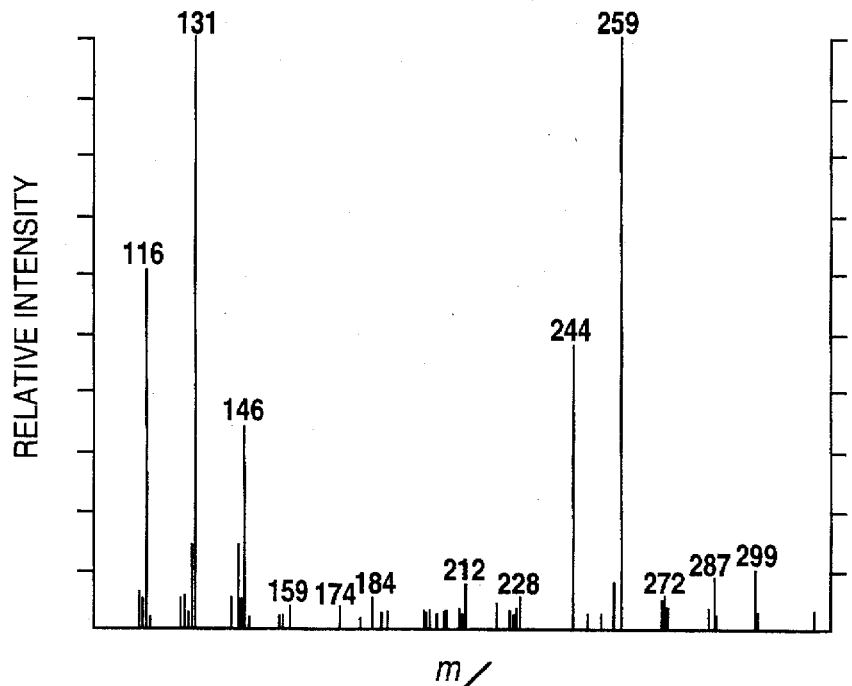
FIGS. 3A–3B, show the CI mass spectra of TLC fractions with NK toxic activity and of synthetic Leu-Leu-OMe.

The nature of the new TLC peak found as described in Example 4 was examined by mass spectroscopy. As shown in FIG. 3A, when the TLC-purified, NK-toxic fraction was subjected to mass spectral analysis, results showing peaks at M/2 259 (MN+), 287 (M+C$_2$H$_5$+) and 299 (M+C$_3$H$_5$+)) indicated the presence of a compound of molecular weight 258. The presence of peaks at M/Z 244 (M⁺—CH$_3$) and 272 (M+C$_2$H$_5$⁺—CH$_3$) suggested that this compound contained a methyl ester group. Furthermore, the persistence of peaks corresponding to leucine (MN⁺=131, M+C$_2$H$_5$=159) and leucine methyl ester (MH⁺=146, M+C$_2$H$_5$⁺=174), in spite of careful TLC purification of the NK toxic product from any free leucine or Leu-OMe present in the crude supernatants of the incubation mixtures, suggested that a condensation product of Leu-OMe such as Leu-Leu-OMe (MW258) was present in the NK toxic fraction isolated after incubation of PMN or MP with Leu-OMe.

When Leu-Leu-OMe was synthesized from reagent grade Leu-Leu, by incubation in methanol hydrochloride, it was found to have TLC mobility identical to NK toxic fractions of MP-Leu-OMe or PMN-Leu-OMe incubation mixtures. Furthermore, its CI mass spectrum as shown in FIG. 3B was identical to that of the 258 molecular weight compound found in these incubation fractions.

Experiments further confirmed that Leu-Leu-OMe was the product generated by MP or PMN from Leu-OMe that was responsible for the selective ablation of NK function from human lymphocytes. Leu-Leu-OMe was synthesized by addition of Leu-Leu to methanolic HCl. TLC analysis revealed less than 2% contamination of this preparation with leucine, Leu-Leu, or leu-OMe, and CI mass spectral analysis (FIG. 3B) revealed no contaminants of other molecular weights.

Figure 3B:
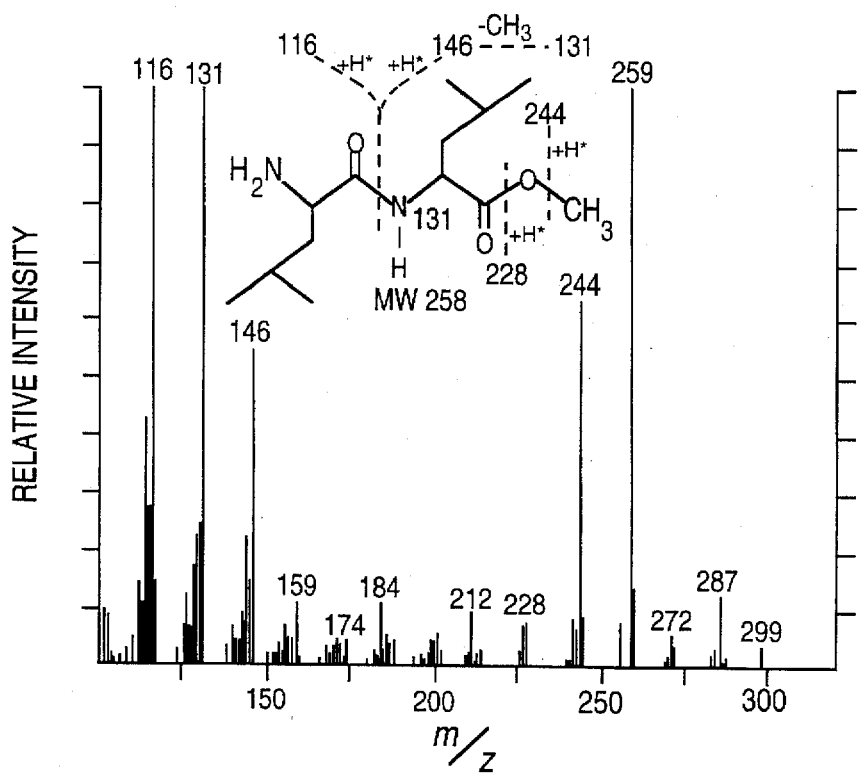

FIG. 3A shows the chemical-ionization CI mass spectra of TLC fractions with NK toxic activity as described in FIG. 2, and also of Leu-Leu-OMe synthesized from reagent grade Leu-Leu (FIG. 3B).

EXAMPLE 6

Figure 4A:
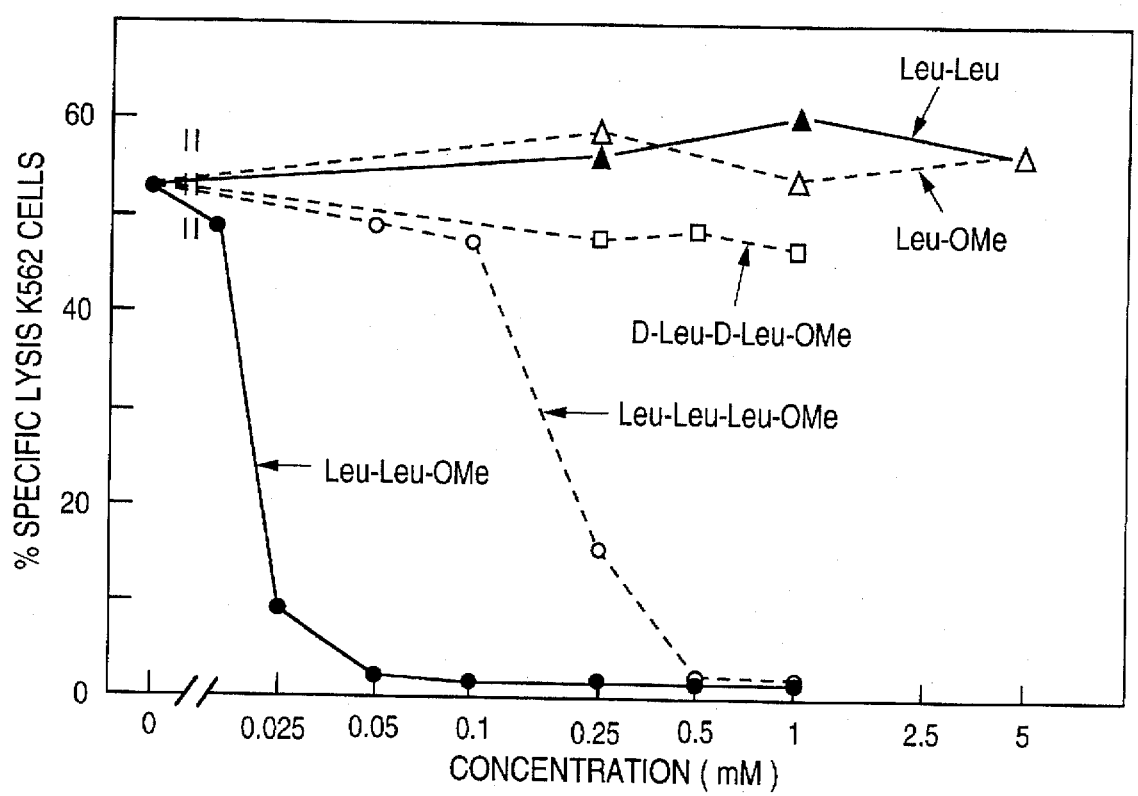
FIGS. 4A–4B show the effects of various agents on losses of NK function from MP-depleted lymphocytes.
Figure 4B:
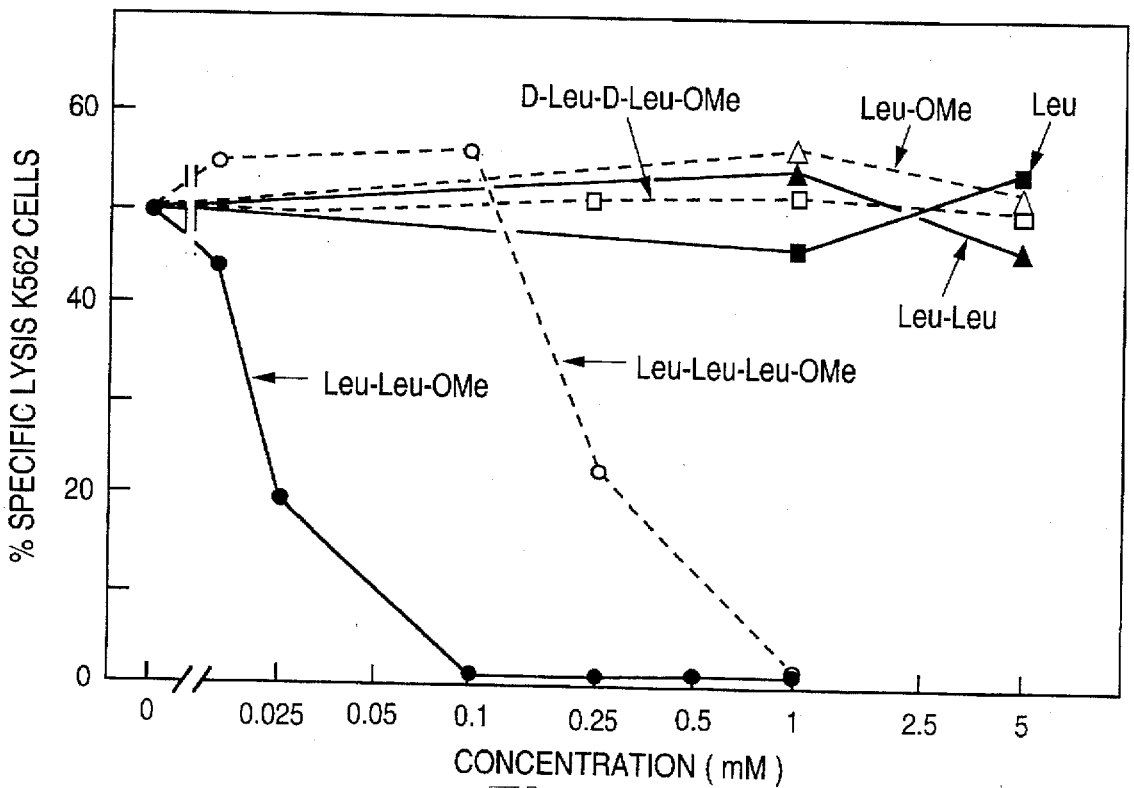

In the representative experiments shown in FIG. 4, MP-depleted lymphocytes were exposed to varying concentrations of Leu-Leu-OMe for 15 minutes at room temperature, then washed and assayed for ability to lyse K562 cells. No NK function could be detected in lymphocyte populations exposed to greater than 50 micromolar Leu-Leu-OMe. As previously demonstrated (Thiele et al. (1983) J. Immunol. V 131 pp 2282-2300), exposure of such MP-depleted lymphocyte populations to 100 fold greater concentration of leucine or leu-OMe had no irreversible effect on NK function. Leu-Leu or the D-stereoisomer, D-Leu-D-Leu-OMe, also had no inhibitory effect. While Leu-Leu-Leu-OMe caused dose-dependent loss of NK function, 5-fold greater concentrations of this tripeptide methyl ester were required to cause an effect equivalent to that of the dipeptide methyl ester of L-leucine. When lymphocyte populations exposed to varying concentrations of Leu-Leu-OMe were further analyzed, it was found that exposure to more than 50 micromolar Leu-Leu-OMe resulted in the loss of K562 target binding as well as complete depletion of cells stained by an anti-NK cell monoclonal antibody Leu 11b. Thus, the MP-or PMN-generated product of Leu-OMe which is directly toxic for human NK cells is the dipeptide condensation product Leu-Leu-OMe.

The condition of the manipulations resulting in the data leading to FIG. 4 are further detailed as follows: for loss of NK function after exposure to Leu-Leu-OMe, MP-depleted lymphocytes ($2.5\times10^6$ cells/ml) were incubated for 15 minutes with the indicated concentrations of leucine containing compounds. Cells were then washed, cultured at 37~C. for 2 hours (Expt. 1) or 18 hours (Expt. 2) and then assayed for NK activity. Results are given for E:T ratio of 20:1.

EXAMPLE 7

NK Ablation by a Variety of Dipeptide Methyl Esters

Figure 5A:
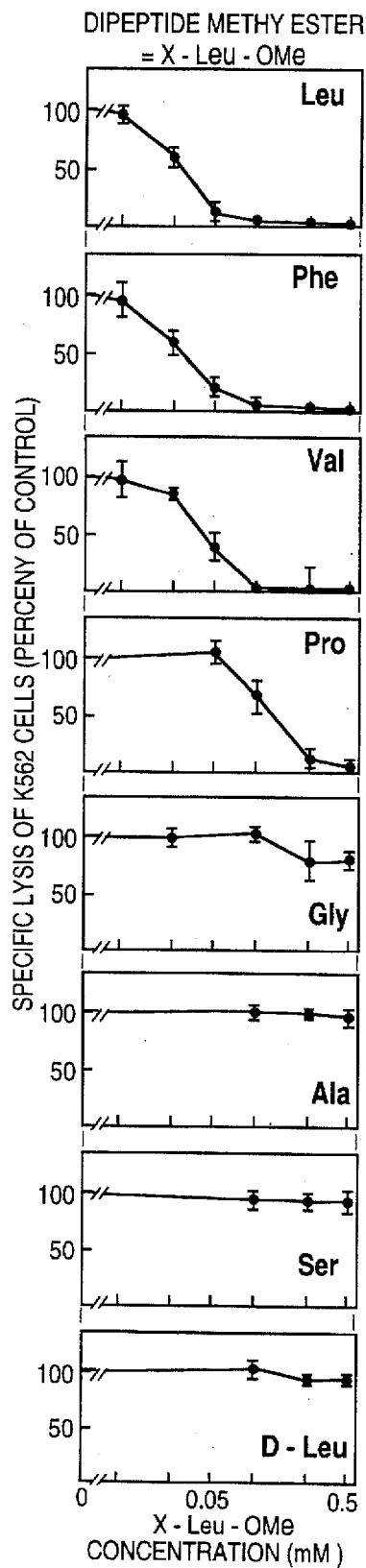
FIGS. 5A–5C show the NK-toxicity of various dipeptide esters.
Figure 5B:
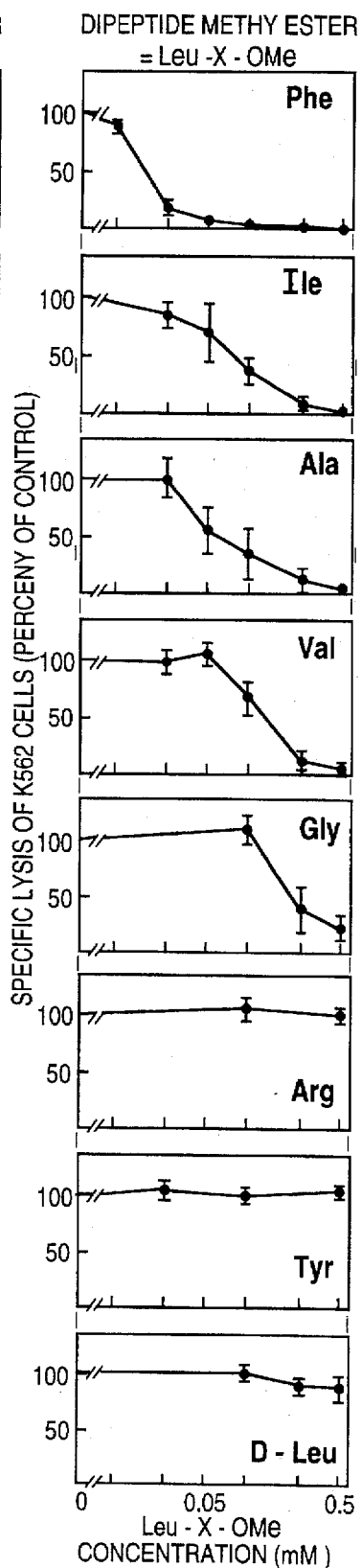
Figure 5C:
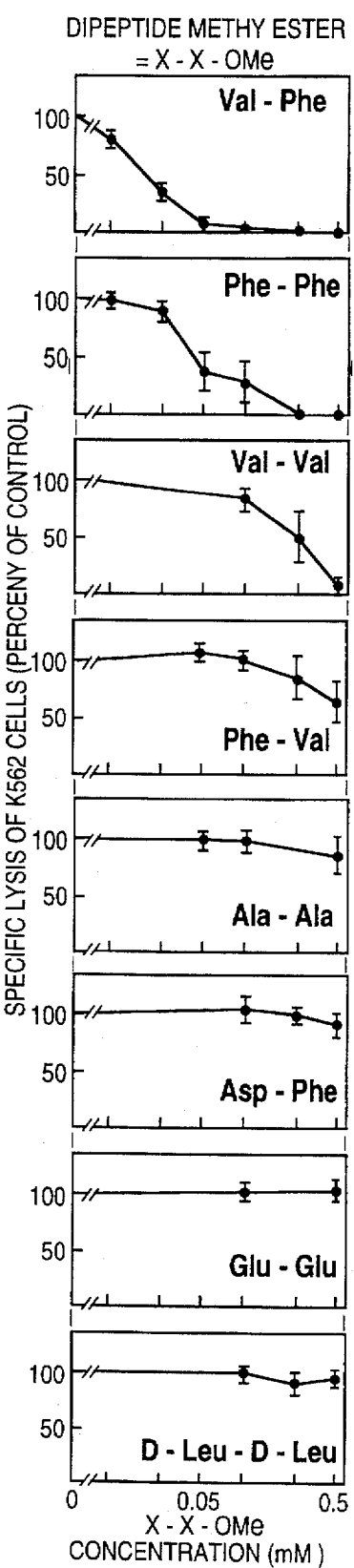

In previously reported studies, Leu-OMe was unique among a wide variety of amino acid methyl esters in its ability to cause MP or PMN dependent ablation of NK cell function from human PBM (Thiele et al. (1985) J. Immunol. V 134, pp 786–793). The identification of Leu-Leu-OMe as the MP-generated metabolite responsible for this phenomenon suggested that either MP/PMN did not generate the corresponding dipeptide methyl esters in toxic amounts from other amino acids, or that Leu-Leu-OMe was unique among dipeptide methyl esters in its toxicity for NK cells. Therefore, experiments were carried out to assess the effect of other dipeptide methyl esters on NK cell function. The methyl esters of a variety of dipeptides were synthesized and analyzed for the capacity to deplete NK Cell function. Each dipeptide methyl ester was assessed in a minimum of three experiments. As is shown by the results displayed in FIG. 5, Leu-Leu-OMe is not the only dipeptide methyl ester which exhibits NK toxicity. When amino acids with hydrophobic side chains were substituted for leucine in either position, the resulting dipeptide methyl ester generally displayed at least some degree of NK toxicity. In particular, Leu-Phe-OMe, Phe-Leu-OMe, Val-Phe-OMe, and Val-Leu-OMe produced concentration-dependent ablation of NK function at concentrations comparable to those at which Leu-Leu-OMe was active. The sequence of active amino acids was important, however, as evidenced by the finding that Phe-Val-OMe was markedly less active than Val-Phe-OMe. Similarly, Leu-Ala-OMe was NK inhibiting, whereas 10-fold greater concentrations of Ala-Leu-OMe had no NK inhibitory effects. Furthermore, Phe-Phe-OMe was less NK toxic than either Leu-Phe-OMe or Phe-Leu-OMe and Val-Val-OMe was less active than either Leu-Val-OMe or Val-Leu-OMe, yet Val-Phe-OMe was among the most potent of the NK toxic dipeptide methyl esters. Thus, conformational aspects of the dipeptide methyl ester amino acid side chain also seem to be of importance in producing the different levels of observed NK toxicity. When amino acids with hydrophilic, charged or hydrogen side chains were substituted for leucine, the resulting dipeptide methyl esters either had greatly reduced NK toxicity, as in the case of Gly-Leu-OMe or Leu-Gly-OMe, or no observed NK inhibitory effects, as in the case of Leu-Arg-OMe, Leu-Tyr-OMe, Ser-Leu-OMe, Lys-Leu-OMe or Asp-Phe-OMe. Furthermore, when the D-stereoisomer was present in either position of a dipeptide methyl ester, no toxicity was observed for NK cells (FIG. 5). When unesterified dipeptides were assessed for their effect on NK function, as in the case of Leu-Leu (FIG. 4), up to $5\times10^{-3}$M concentrations of Leu-Phe, Phe-Leu, Val-Leu, and Val-Phe had no effect on NK cell survival or lytic activity.

D-Leu-D-Leu-OMe had no effect on Leu-Leu-OMe mediated NK toxicity although high levels of zinc appeared to inhibit this Leu-Leu-OMe toxicity.

Previous experiments had demonstrated that compounds such as Val-OMe, Phe-OMe, or combinations of Val-OMe and Phe-OMe did not delete NK function from human PBM (Thiele et al. (1985) J. Immunol. V 134, pp 786–793), despite the current finding that dipeptide methyl esters containing these amino acids were potent NK toxins. In order to determine whether MP or PMN could generate the relevant dipeptide methyl esters from these amino acid methyl esters, TLC analysis of the supernatants of MP and PMN incubated with these compounds was carried out. It was found that MP and PMN did generate detectable amounts of dipeptide methyl esters from these L-amino acid methyl esters. However, when equal concentrations of Leu-OMe, Val-OMe, or Phe-OMe were added to MP or PMN, the concentrations of Val-Val-OMe generated were 50 to 80% of those found for Leu-Leu-OMe, while Phe-Phe-OMe was detected at only 10–30% of the levels of Leu-Leu-OMe. Dipeptide methyl esters were not generated from D-amino acid methyl esters.

FIG. 5 shows the NK toxicity of dipeptide methyl esters. MP-depleted lymphocytes were treated with varying concentrations of dipeptide methyl esters as outlined in FIG. 4. Results are given for the mean ±SEM of at least 3 separate experiments with each compound.

EXAMPLE 8

NK Toxicity of an Artificially Hydrophobic Dipeptide Methyl Ester

Beta methyl aspartyl phenylalanine was prepared by methanolic hydrochloride methylation of aspartyl phenylalanine methyl ester. The NK toxicity of both aspartyl phenylalanine methyl ester and beta methyl aspartyl phenylalanine methyl ester was measured as described for the dipeptide methyl esters in Example 7. As the data in Table 2 indicates, when the polar side chain of the aspartyl amino acid dipeptide component is esterified with a methyl group, this being a conversion from relative hydrophilicity to substantial hydrophobicity, NK toxicity becomes apparent. Although yet not as toxically effective as a number of the hydrophobic-type dipeptides in Example 7, the data in Table 2 indicate that a dipeptide methyl ester comprising synthetic hydrophobic (lipophilic) amino acids may be used to inhibit NK function.

TABLE 2

L-ASPARTYL (beta-METHYL ESTER)-L-PHENYLALANINE METHYL ESTER IS NK TOXIC WHILE L-ASPARTYL-L-PHENYLALANINE METHYL ESTER IS NOT

| Preincubation | NK Function % Specific Cytotoxicity |
|---|---|
| Nil | 50.8 |
| Asp—Phe—OMe: | |
| 100 micromolar | 54.2 |
| 250 micromolar | 45.7 |

TABLE 2-continued

L-ASPARTYL (beta-METHYL ESTER)-L-PHENYLALANINE METHYL ESTER IS NK TOXIC WHILE L-ASPARTYL-L-PHENYLALANINE METHYL ESTER IS NOT

| Preincubation | NK Function % Specific Cytotoxicity |
|---|---|
| 500 micromolar | 45.7 |
| 1000 micromolar | 46.9 |
| Asp—(beta—OMe)—Phe—OMe: | |
| 100 micromolar | 38.9 |
| 250 micromolar | 13.9 |
| 500 micromolar | 2.8 |
| 1000 micromolar | −0.1 |

EXAMPLE 9

In Vivo Effects on Cytotoxic Cell Function

Leu-Leu-OMe or Leu-Phe-OMe were suspended in PBS, pH 7.4. Then individual $C_3H/HeJ$ mice (25 gram size) were administered by tail-vein injection either $2.5\times10^{-5}$ moles (6.5 mg) of Leu-Leu-OMe, $2.5\times10^{-5}$ moles (7.1 mg) Leu-Phe-OMe, or an equal volume of the PBS diluent, this dose being about $1\times10^{-3}$ moles per kg. For 15–30 minutes post-injection, Leu-Leu OMe and Leu-Phe OMe-treated animals but not the control animals exhibited decreased activity and an apparent increase in sleep. Subsequent to this quiescent period no difference in activity or appearance in the mice was noted. Two hours post-injection, the mice were sacrificed and their spleen cells were assayed for NK function in a standard 4 hour assay against YAC-1 tumor targets. In all mice, total cell recovery ranged from $1\times10^8$ to $1.1\times10^8$ spleen cells per animal. As noted in Table 3, the control mouse spleen cells exhibited greater killing at 25:1 and 50:1 effector to target cell ratios than did the spleen cells of treated mice at 100:1 and 200:1 E/T, respectively. Thus, Leu-Leu-OMe or Leu-Phe-OMe caused a greater than 75% decrease in splenic lytic activity against YAC-1 tumor targets.

TABLE 3

| | Cytotoxic Cell Function | | | |
|---|---|---|---|---|
| Effector:Target Ratio | 25:1 | 50:1 | 100:1 | 200:1 |
| | Percent lysis of target cells | | | |
| Control | 8.29 | 12.88 | 20.60 | 29.29 |
| Leu—Leu—OMe | 2.37 | 4.58 | 7.12 | 12.77 |
| Leu—Phe—OMe | 3.89 | 4.68 | 6.91 | 11.91 |

EXAMPLE 10

Differential Sensitivity of Natural Killer Cells (NK) and Mononuclear Phagocytes (MP) to Leucylleucine-Methyl Ester (Leu-Leu-OMe)

Figure 6:
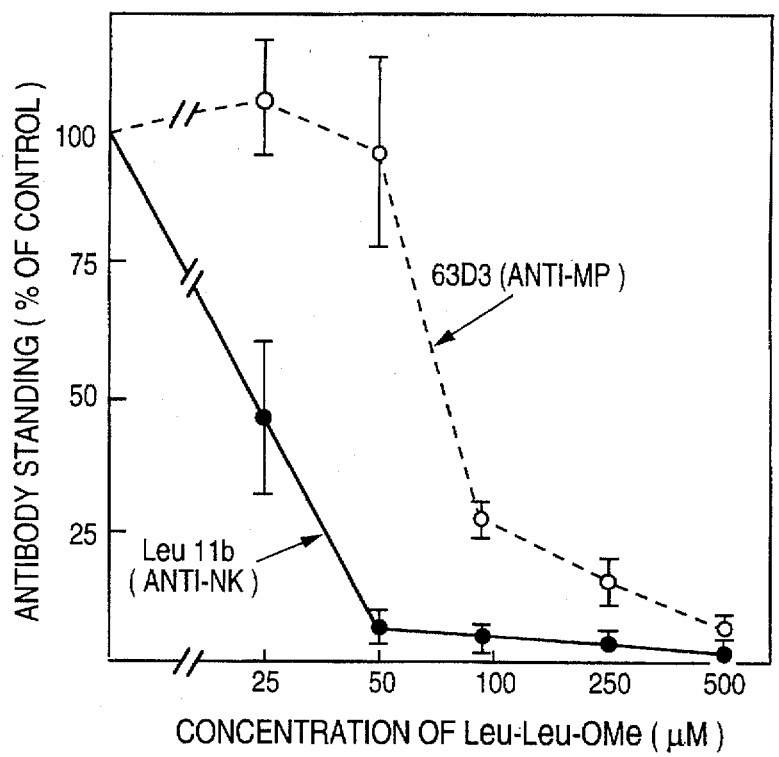
FIG. 6 shows the loss of NK and MP from PBM incubated with Leu-Leu-OMe at various concentrations.

In the experiments depicted in FIG. 6, freshly isolated PBM ($2.5\times10^6$/ml PBS and 1 g/l glucose) were incubated at room temperature with varying concentrations of Leu-Leu-OMe. After a 15 minute exposure to this compound, the cells were washed, incubated for 2 hours at 37° C. and then assessed for the percentage of remaining viable cells which were stained by anti-MP or anti-NK monoclonal antibodies. Preincubation with greater than 25–50 micromolar Leu-Leu-OMe led to loss of NK cells. This concentration of Leu- Leu-OMe did not deplete MP from PBM but higher concentrations of Leu-Leu-OMe caused loss of MP. The data is FIG. 6 show these results.

Anti-MP monoclonal antibodies (63D3) and anti-NK monoclonal antibodies (leu 11b) were obtained from Becton Dickinson Monoclonal Center, Inc., Mountain View, Calif. The antibody staining and Fluorescence Activated Cell Sorter (FACS) procedure was that of Rosenberg et al. (1981) (J. Immunol. V 126, p 1473). Data are expressed as percent of antibody staining in control cells (mean ±SEM, n=4).

EXAMPLE 11

Effects of Leu-Leu-OMe on a Variety of Cell Types

While it was clear that a substantial percentage of lymphocytes remained viable following exposure to even 1 mM Leu-Leu-OMe, the finding that disparate cell types such as MP and NK were both susceptible to Leu-Leu-OMe mediated toxicity raised the possibility that this agent was a non-specific cell toxin. Therefore, the series of experiments depicted in FIG. 7 was performed to assess other cell types for evidence of toxicity following exposure to Leu-Leu-OMe.

To facilitate screening of multiple cell types for evidence of cell death following exposure to Leu-Leu-OMe, a $^{51}$Cr release assay was devised. In preliminary experiments it was noted that $^{51}$Cr release from MP-enriched populations exposed to varying concentrations of Leu-Leu-OMe correlated very closely with concentration-dependent loss of anti-MP antibody staining cells from PBM after similar incubation. Following brief exposures to Leu-Leu-OMe at room temperature, the loss of anti-MP antibody staining cells from PBM or the release of $^{51}$Cr from MP-enriched populations was always detectable within a 30 to 60 minute period of culture at 37° C. and maximal effects were seen within 3 to 4 hours.

Therefore, $^{51}$Cr release in a 4 hour assay was used in these experiments to assess toxicity from Leu-Leu-OMe. As shown in the first graph of FIG. 7, when the whole PBM population was exposed to varying concentrations of Leu-Leu-OMe, detectable $^{51}$Cr release was observed after exposure to 25 to 50 micromolar Leu-Leu-OMe, but only upon exposure to greater than 100 micromolar Leu-Leu-OMe was the maximal achievable $^{51}$Cr release from PBM observed. When MP-enriched adherent cells (AC) were similarly assessed, minimal $^{51}$Cr release was observed after exposure to 25-50 micromolar Leu-Leu-OMe whereas upon incubation with higher concentrations of this agent, more $^{51}$Cr release from AC was observed than with PBM. When nylon wool non-adherent lymphocytes (NAC) were assessed, small but significant $^{51}$Cr release was observed with 25 to 50 micromolar Leu-Leu-OMe. When NAC were exposed to increasing concentrations of Leu-Leu-OMe, greater quantities of $^{51}$Cr release were observed. N-SRBC positive cells showed a dose-dependent Leu-Leu-OMe induced $^{51}$Cr release pattern indistinguishable from that of NAC. Since both antibody staining (FIG. 6) and functional studies (FIG. 4) have shown that 100 micromolar Leu-Leu-OMe causes maximal depletion of NK, this finding suggested that other lymphocytes were also susceptible to Leu-Leu-OMe toxicity at concentrations greater than 100 micromolar. When T4 enriched populations of T cells were assessed, however, it was clear that even 1000 micromolar Leu-Leu-OMe caused minimal $^{51}$Cr release from this population. In Contrast, when N-SRBC positive cells were depleted of OKT4 positive cells, the remaining T8-enriched population produced high levels of $^{51}$Cr release following exposure to Leu-Leu-OMe.

When cell lines of myeloid or lymphoid origin were similarly assessed, selective toxicity of Leu-Leu-OMe was again observed. The human T cell leukemia line MoLT-4 demonstrated no detectable Leu-Leu-OMe toxicity over a broad concentration range. The human plasma cell lines HS-Sultan and the B tymphoblastoid line Daudi demonstrated no significant $^{51}$Cr release or alteration in subsequent proliferative rate (data not shown) after exposure to a broad range of Leu-Leu-OMe concentrations. When the susceptibility of EBV-transformed B cell lines or clones to this agent was assessed, no significant toxicity of less than 250 micromolar Leu-Leu-OMe was seen. However, with higher concentrations of Leu-Leu-OMe, a variable degree of toxicity was seen. Some EBV lines consistently displayed less than 20% $^{51}$Cr release even after exposure to 1 mM Leu-Leu-OMe, while other lines produced 25–35% $^{51}$Cr release after exposure to 250 micromolar Leu-Leu-OMe. In contrast, the human cell line U937 was susceptible to concentration-dependent Leu-Leu-OMe toxicity in a pattern indistinguishable from that of the peripheral blood MP with which this cell line shares many phenotypic and functional characteristics. After exposure to more than 250 micromolar Leu-Leu-OMe, extensive $^{51}$Cr release was observed and no viable proliferating U937 cell could be detected (data not shown). Similarly, the erythroleukemia line K562 demonstrated no significant $^{51}$Cr release or alteration in subsequent proliferative rate (date not shown) upon exposure to 100 micromolar or lower concentrations of Leu-Leu-OMe. With higher concentrations of Leu-Leu-OMe, modest amounts of $^{51}$Cr release and partial loss of proliferative capacity were observed (data not shown). In contrast, a variety of cell types of non-lymphoid, non-myeloid origin including human umbilical vein endothelial cells, the human renal cell carcinoma line, Currie, the human epidermal carcinoma line, HEp-2, and human dermal fibroblasts demonstrated no significant Leu-Leu-OMe induced $^{51}$Cr release. Furthermore, incubation of each of these non-lymphoid cell types with 500 micromolar Leu-Leu-OMe had no discernible effect on subsequent proliferative capacity (data not shown).

HS-Sultan, a human plasma cell line (Goldblum et al. (1973) Proc. Seventh Leucocyte Culture Conference, ed by Daguilland, Acad. Press N.Y. pp 15–28), Daudi, a B lymphoblastoid cell line (Klein et al. (1968) Cancer Res. V 28, p 1300), MoLT-4, an acute lymphoblastic T-cell leukemia line (Monowada et al. (1972) J. Nat'l. Canc. Inst. V 49, p 891), and U-937, a human monocyte-like cell line (Koren et al. (1979) Nature V 279, p 891) were obtained from the American Type Culture Collection, Rockville, Md. These lines as well as HEp-2 a human epidermoid carcinoma line (a generous gift of Dr. R. Sontheimer, UTHSCD); Currie, a human renal cell. carcinoma line (a generous gift of Dr. M. Prager, UTHSCD); and K562, a human erythroleukemia line (a generous gift of Dr. M. Bennett, UTHSCD) were maintained in culture in medium RMPI supplemented with 10% FBS. Human dermal fibroblasts (a generous gift of Dr. T. Geppert, UTHSCD) were serially passaged in culture as well while human umbilical vein endothelial cells (a generous gift of Dr. A. Johnson, UTHSCD) were used after one subculture. Epstein Barr virus (EBV) transformed B lymphoblastoid cell lines JM.6 and SM.4 (kindly provided by Dr. J. Moreno, UTHSCD) and cloned EBV transformed B cell lines SDL-G2 and D8-219 (a generous gift of Drs. L. Stein and M. Dosch, Hospital for Sick Children, Toronto, Canada) were maintained in culture in medium RPMI supplemented with 10% FBS.

In some experiments, toxicity of Leu-Leu-OMe for a variety of cell populations was assessed by $^{51}$Cr release. In assays where cells obtained from suspension culture were to be used, cells were labeled with $Na_2{}^{51}CrO_4$ (ICN, Plainview, N.Y.) for 60–90 minutes at 37° C. and then washed three times. Cells were then suspended in PBS ($2.5\times10^6$/ml) and incubated in microtiter plates, 50 microL/well with indicated concentrations of Leu-Leu-OMe for 15 minutes at room temperature. In assays where cells were obtained from monolayer cultures, microtiter wells were seeded with cells ($5\times10^4$/well) and cultured for 24 hours at 37~C. Cells were then labeled with $Na_2{}^{51}CrO_4$ while in adherent culture. Following $^{51}$Cr labeling, wells were thoroughly washed and varying concentrations of Leu-Leu-OMe added in 50 microL PBS and the plates incubated for 15 minutes at room temperature.

Following such initial serum-free incubations, 200 microL/well of medium RPMI containing 10% FBS were added and the plates incubated for another 4 hours prior to removal of 100 microliters of supernatant. Radioactivity in the supernatant was measured in an auto-gamma scintillation spectrometer (Packard Instrument Co., Downers Grove, Ill.). The percent specific release was calculated from the formula:

$$\% \text{ spec. release (rel)} = \frac{\text{exp. rel (cpm)} - \text{spont. rel (cpm)}}{\text{max. rel (cpm)} - \text{spont. rel (cpm)}}$$

in which maximal release refers to cpm obtained in Wells containing 50% lysing agent (American Scientific Products, McGraw Park, Ill.) and spontaneous release refers to cpm released by cells incubated in control medium in the absence of Leu-Leu-OMe or the lysing agent. Only experiments in which spontaneous release was 25% were used for subsequent data interpretation.

While the MP-like tumor line U937 was virtually identical to MP in susceptibility to Leu-Leu-OMe, none of the non-lymphoid, non-myeloid cell lines tested demonstrated such susceptibility to Leu-Leu-OMe mediated toxicity.

The current example demonstrates that at concentrations 10 to 20 fold greater than those at which cytotoxic cells are ablated, Leu-Leu-OMe does have some minimal toxicity for certain non-cytotoxic lymphoid cells such as EBV transformed B cells and K562 cells. Yet, while it is impossible to exhaustively exclude the possibility that certain non-cytotoxic cells might also be equally sensitive to Leu-Leu-OMe-mediated toxicity, at present the ability to function as a mediator of cell mediated cytotoxicity is the one unifying characteristic of the cell types which are rapidly killed by exposure to Leu-Leu-OMe.

Figure 7:
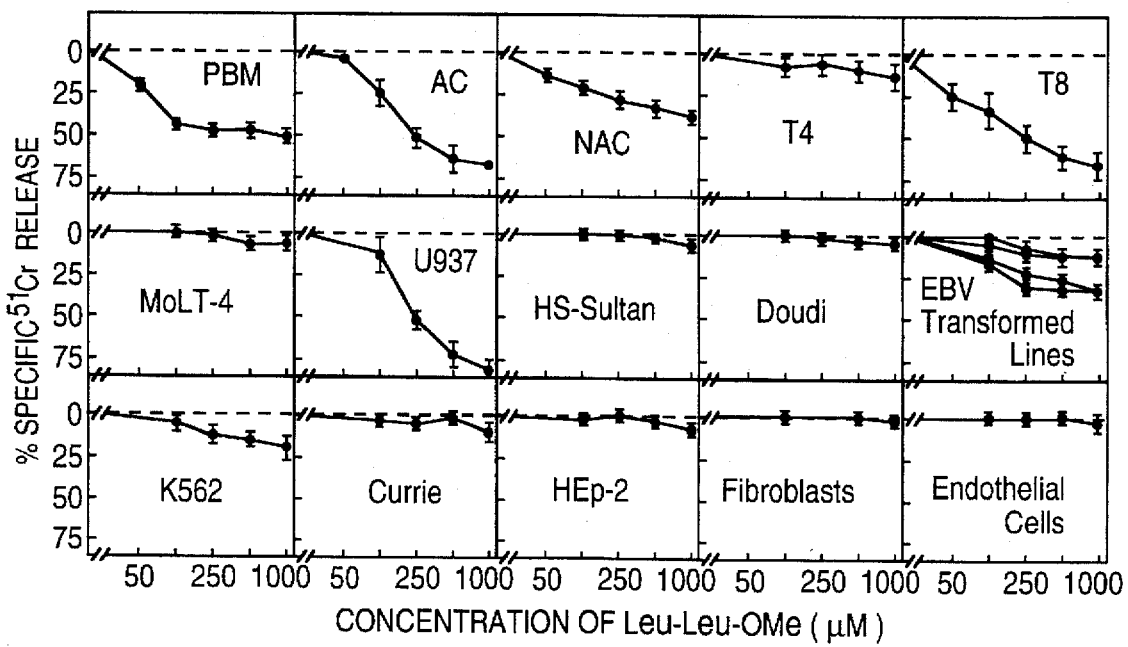
FIG. 7 shows the toxicity of various Leu-Leu-OMe concentrations for selected cell types.

In developing the data expressed in FIG. 7, cells ($2.5\times10^6$/ml) were exposed to the indicated concentrations of Leu-Leu-OMe for 15 minutes at room temperature, then specific $^{51}$Cr release during the next four hours was assessed. Data for the EBV transformed lines JM.6, SDLG2, D8-219, and SM.4, respectively, are shown in order from top to bottom.

EXAMPLE 12

Relative Sensitivity of CTL and NK to Leu-Leu-OMe

Figure 8:
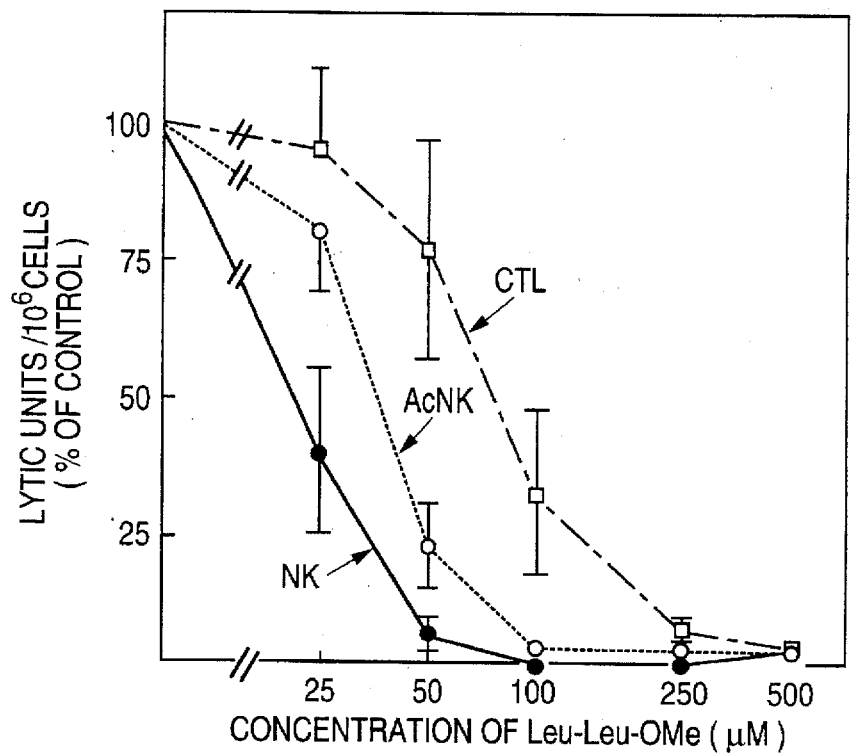
FIG. 8 shows the Leu-Leu-OMe mediated elimination of precursors of cytotoxic T lymphocytes activated NK ($A_cNK$) and FIG. 9 shows the sensitivity of activated NK and CTL to treatment with Leu-Leu-OMe.

Experiments were also designed to assess the relative sensitivity of NK and CTL to Leu-Leu-OMe. In the studies detailed in FIGS. 8 and 9, cytotoxicity assays were performed over a broad range of E:T ratios and units of lytic activity arising from equal numbers of responding lymphocytes were calculated and compared. As shown in FIG. 8, both spontaneous NK and precursors of activated NK were totally eliminated by exposure to 100 micromolar Leu-Leu-OMe while CTL precursors, though diminished, were generally still present at greater than 50% of control levels. Only after exposure to greater than 250 micromolar Leu-Leu-OMe were all CTL precursors eliminated.

FIG. 8 shows that incubation with Leu-Leu-OMe eliminates precursors of cytotoxic T lymphocytes (CTL) and activated NK-like cells ($A_cNK$). Non-adherent lymphocytes ($2.5\times10^6$/ml) were incubated with the indicated concentrations of Leu-Leu-OMe for 15 minutes. Cells were then washed and either placed in mixed lymphocyte culture or assayed for specific lysis of K562 cells (NK). After 6 day MLC, cells were assayed for specific lysis of allogeneic stimulator lymphoblasts (CTL) or K562 ($A_cNK$). Data are expressed as percent of control lytic units (mean+SEM, n=6).

Figure 9:
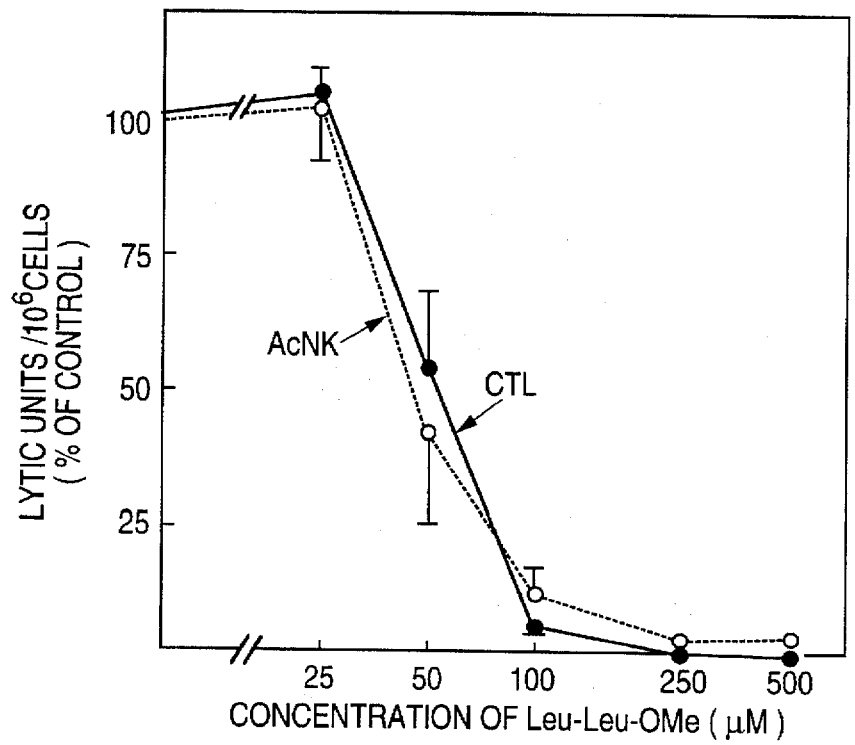

When the elimination of CTL and activated NK precursors by Leu-Leu-OMe was compared to that of spontaneous NK, the mean Leu-Leu-OMe concentration required to diminish lytic activity by 75% was significantly greater for elimination of CTL precursors (123±25 micromolar) than for elimination of precursors of activated NK (50±5 micromolar, p 0.05). Both values were also higher than the mean concentration of Leu-Leu-OMe required to diminish spontaneous NK lytic activity by 75% (35 micromolar±4 micromolar). FIG. 9 shows that, following activation, CTL and $A_cNK$ became identical in sensitivity to Leu-Leu-OMe. After 6 day MLC, cells were incubated for 15 minutes with the indicated concentrations of Leu-Leu-OMe, then assayed for CTL or $A_cNK$ activity as for FIG. 8. Thus, only after MLC activation did CTL display a sensitivity to Leu-Leu-OMe toxicity that was equal to that of NK cells.

EXAMPLE 13

Mechanism of Leu-Leu-OMe

Prior Examples demonstrated that incubation of mixed lymphoid cell populations with L-leucyl-L-leucine methyl ester (Leu-Leu-OMe) results in selective loss of NK cells and precursors of cytotoxic T cells whereas B cell and T helper cell function is relatively preserved. Of note, use of Leu-Leu-OMe to remove donor cytotoxic lymphocytes has been shown to be of benefit in preventing lethal graft-versus-host disease in a murine model of allogeneic bone marrow transplantation. The present example involves elucidation of the mechanism whereby Leu-Leu OMe kills cytotoxic lymphocytes.

Figure 10:
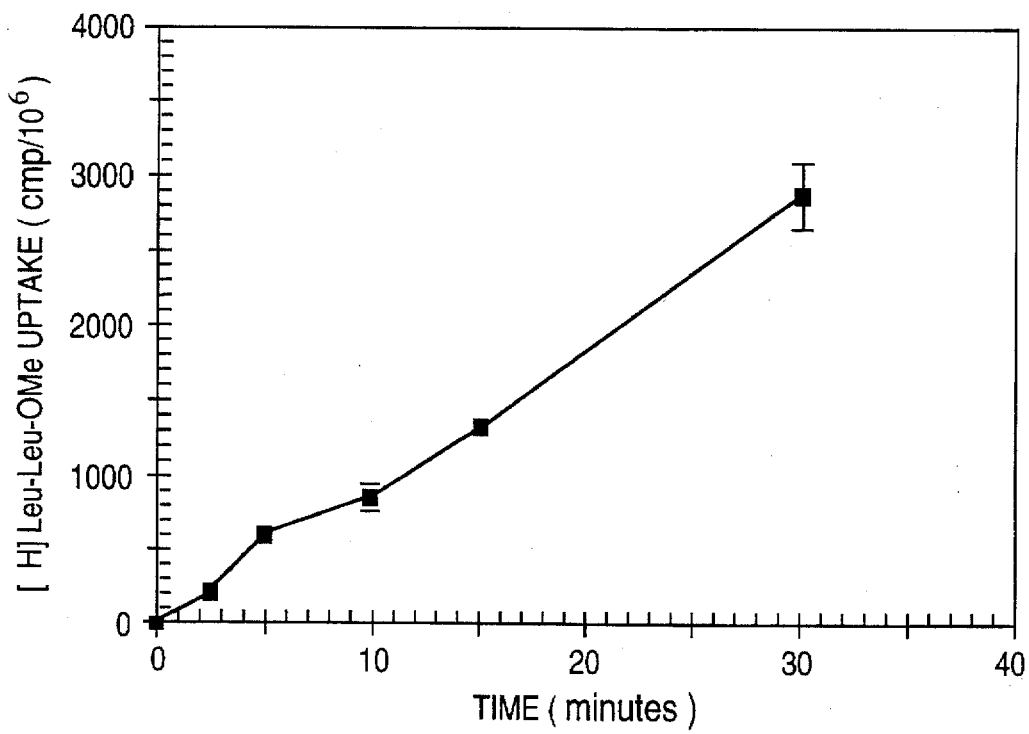
FIG. 10 shows the time-dependent uptake of Leu-Leu-OMe by PBL.

Human peripheral blood lymphocytes (PBL) were incubated in the presence of [$^3$H]labeled Leu-Leu-OMe at 22° C. for varying lengths of time. The incubation mixture was then centrifuged through silicone oil to separate the cells from any unbound or non-internalized [$^3$H]Leu-Leu-OMe. As demonstrated in FIG. 10, the quantity of cell-associated [$^3$H]Leu-Leu-OMe increased in a linear, time-dependent fashion over the first 30 minutes of incubation. As demonstrated in Table 4, when incubations were performed at temperatures below 4~C., no accumulation of [$^3$H]Leu-Leu-OMe by PBL was observed. At 37° C., levels of [$^3$H]Leu-Leu-OMe accumulation by PBL were increased above those seen at 22° C. (see Table 4). These findings suggested that Leu-Leu-OMe was not simply binding to PBL by an energy (temperature) independent process. The time and temperature dependent increases in cell-associated [³H]labeled Leu-Leu-OMe suggested that this compound was being internalized and retained by PBL.

TABLE 4

TEMPERATURE DEPENDENCE OF [³H]LEU—LEU—OME UPTAKE/BINDING BY LYMPHOCYTES

| Expt. | Temperature | [³H]Leu—Leu—OMe Uptake/Binding (micro-moles/10⁶ cells) |
|---|---|---|
| 1 | 0° C. | 0.05 |
|   | 22° C. | 0.77 |
| 2 | 4° C. | 0.02 |
|   | 22° C. | 0.31 |
|   | 37° C. | 0.52 |

Figure 11:
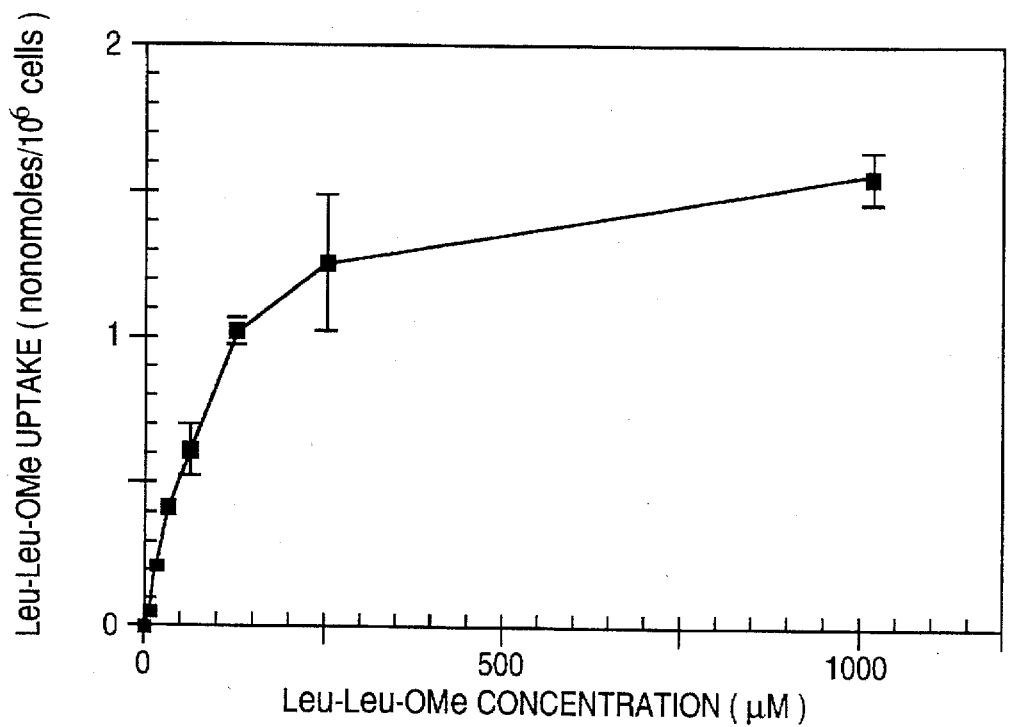
FIG. 11 shows the concentrations dependence of Leu-Leu-OMe uptake by PBL.

When the concentration dependence of Leu-Leu-OMe uptake by PBL was assessed (see FIG. 11), the quantity of [³H]Leu-Leu-OMe incorporated per unit of time was noted to increase in direct proportion to external concentrations until near maximal uptake was noted with approximately 250–500 micro-M. The findings detailed in FIG. 11 indicate the uptake of Leu-Leu-OMe observed after a 15 minute incubation performed at 22° C. The data indicate that under these conditions the Vmax of (maximum velocity) this process is approximately $10^{-10}$ moles/minute/$10^6$ cells, whereas the Km is approximately $10^{-4}$M. These findings indicate that this process is saturable and therefore a facilitated transport mechanism is likely to be involved in the uptake of Leu-Leu-OMe by PBL. As demonstrated by the results displayed in Table 5, [³H]Leu-Leu-OMe uptake by PBL is competitively inhibited not only by excess quantities of unlabeled Leu-Leu-OMe, but also by high concentrations of the dipeptide Leu-Leu and by other esters of Leu-Leu such as Leu-Leu-OBenzyl.

TABLE 5

COMPETITIVE INHIBITION OF [³H]LEU—LEU—OME UPTAKE BY OTHER DERIVATIVES OF LEU—LEU

| Unlabeled Compound* | % Inhibition of [³H]Leu—Leu—OMe Uptake⁺ |
|---|---|
| L—Leu—OMe | −10 |
| L—Leu—Leu | 44 |
| L—Leu—L—Leu—OMe | 72 |
| D—Leu—D—Leu—OMe | 7 |
| L—Leu—L—Leu—OBenzyl | 87 |
| L—Leu—L—Leu—NH₂ | 8 |
| L—Leu—L—Leu—L—Leu—OMe | 6 |

*250 micro-M
⁺10 micro-M

However, the amide derivative of Leu-Leu (L-Leu-L-Leu-NH₂); the D-stereoisomer containing dipeptide ester, D-Leu-D-Leu-OMe; the amino acid analog Leu-OMe; and the tripeptide analog Leu-Leu-Leu-OMe do not competitively inhibit PBL uptake of L-Leu-L-Leu-OMe. Thus, the facilitated transport process utilized by PBL in the uptake of Leu-Leu-OMe appears to be relatively specific for L-stereoisomers of dipeptides or dipeptide esters.

As detailed in Table 6, competitive inhibition of Leu-Leu-OMe uptake is seen with some but not all dipeptide methyl esters composed of L-stereoisomers of naturally occurring amino acids.

TABLE 6

COMPETITIVE INHIBITION OF [³H]LEU—LEU—OME UPTAKE BY OTHER DIPEPTIDE ESTERS

| Unlabeled Compound* | % Inhibition of [³H]Leu—Leu—OMe Uptake⁺ | NK Toxicity (LD₅₀) |
|---|---|---|
| Pro—Leu—OMe | −18 | >250 micro-M |
| Asp—Phe—OMe | 8 | >250 micro-M |
| Leu—Leu—OMe | 72 | 35 micro-M |
| Leu—Phe—OMe | 72 | 29 micro-M |
| Leu—Tyr—OMe | 86 | >250 micro-M |
| Val—Phe—OMe | 75 | 24 micro-M |
| Ser—Leu—OMe | 94 | >250 micro-M |

*250 micro-M
⁺10 micro-M

As previously reported, (see prior examples and PNAS 1985; 82:2468-2472), incubation of PBL for 15 minutes at 22° C. with a variety of dipeptide methyl esters leads to loss of all natural killer cell (NK) function because of the direct toxicity of these compounds for cytotoxic lymphocytes. Concentrations of various dipeptide esters which result in 50% loss of human NK function (LD₅₀) are detailed in the last column of Table 6. Of note, all compounds with significant NK toxicity at concentrations below 250 micro-M appear to be taken up by the same facilitated transport process as evidenced by significant competitive inhibition of [³H]Leu-Leu-OMe uptake. This transport process is not competitively inhibited by some dipeptide esters such as Pro-Leu-OMe or Asp-Leu-OMe. These latter dipeptide esters also exhibit no NK toxicity. Such lack of NK toxicity may be related to lack of accumulation of such agents by NK cells. However, other dipeptide esters such as Leu-Tyr-OMe or Ser-Leu-OMe which display little or no toxicity for NK cells may be, nevertheless, excellent competitive inhibitors of [³H]Leu-Leu-OMe uptake. These findings suggested that characteristics other than capacity for uptake by lymphocytes are likely to be involved in the selective NK toxicity of Leu-Leu-OMe and other dipeptide methyl esters. Whereas uptake by this pathway appears to be necessary for NK cytotoxicity, it is not always sufficient.

Additional experiments, detailed in Table 7, were performed to assess the metabolic fate of [³H]Leu-Leu-OMe within PBL. Cells were incubated with [³H]Leu-Leu-OMe for 15 minutes at 22° C. to permit uptake of this compound and then were washed. If the cells were immediately lysed and 10% trichloroacetic acid (TCA) was added to precipitate higher molecular weight cell proteins and nucleic acids, essentially all of the [³H]label remained in the supernatant as anticipated for a small molecular weight peptide which is soluble in 10% TCA. However, as shown in Table 7, if [³H]Leu-Leu-OMe-loaded PBL were incubated at 37° C. for 15 to 60 minutes prior to cell lysis, an increasing fraction of the [³H] precipitated in 10% TCA.

TABLE 7

[³H]LEU—LEU—OME IS CONVERTED TO A PRODUCT WHICH PRECIPITATES IN THE PRESENCE OF 10% TCA

| Duration of Initial 22° C. Incubation | Duration of Second 37° C. incubation | [³H]Leu—Leu—OMe | |
|---|---|---|---|
|  |  | Total | TCA Prec. |
|  |  | cpm × 10⁻³ | |
| 15 minutes | 0 | 61.4 | 0.5 |
|  | 15 minutes | 24.9 | 6.8 |

TABLE 7-continued

[³H]LEU—LEU—OME IS CONVERTED
TO A PRODUCT WHICH PRECIPITATES
IN THE PRESENCE OF 10% TCA

| Duration of Initial 22° C. Incubation | Duration of Second 37° C. incubation | [³H]Leu—Leu—OMe | |
|---|---|---|---|
| | | Total | TCA Prec. |
| | 30 minutes | 20.6 | 12.7 |
| | 60 minutes | 12.7 | 10.7 |

In other experiments it was noted that addition of proteinase K (e.g. Protease Type XXVIV from Triterochium album, Sigma Chemical Company, St. Louis, Mo.) to the cell lysate prior to TCA precipitation resulted in loss of all [³H]label from the precipitate. These findings suggested that, within the first hour after [³H]Leu-Leu-OMe uptake by PBL, a significant fraction of this peptide or its amino acid components was incorporated into a higher molecular weight form which was insoluble in 10% TCA.

As shown by the data displayed in Table 8 [³H]Leu-Leu-OMe was found to be metabolized differently within various cell populations.

TABLE 8

PRODUCTION OF A TCA PRECIPITABLE PRODUCT FROM
[³H]LEU—LEU—OME DOES NOT CORRELATE WITH
LEVELS OF INITIAL [³H]LEU—LEU—OME
INCORPORATION

| | | [³H]—Leu—Leu—OMe Incorporation | | |
|---|---|---|---|---|
| | | | TCA Precipitate | |
| Expt. | Cell Type | Initial cpm | cpm | (% of initial) |
| 1 | Non-adherent Lymphocytes | 27,870 | 2,341 | 8.4% |
| | LLMe Resistant Lymphocytes | 7,184 | 50 | 0.7% |
| 2 | T4 Cells | 12,200 | 207 | 1.7% |
| | T8, NK Cells | 22,753 | 3,208 | 14.1% |
| | Fibroblasts | 63,229 | 293 | 0.5% |
| | Renal Cell Carcinoma | 35,855 | 267 | 0.7% |

In experiment 1 of Table 8 non-adherent peripheral blood lymphocytes were incubated in the presence or absence of 250 micro-M unlabeled Leu-Leu-OMe for 15 minutes and then cultured overnight at 37° C. This form of exposure to Leu-Leu-OMe has been shown previously herein to result in loss of NK cells and a substantial fraction of CD8(+)T cells, whereas the majority of CD4(+) lymphocytes are resistant to any toxic effects of this agent and remain viable and functionally intact. As shown by the data displayed in Table 8, when these cells were then incubated with [³H]labeled Leu-Leu-OMe for 15 minutes at 22° C., both populations of lymphocytes were observed to take up this compound although uptake by Leu-Leu-OMe (LLMe) resistant lymphocytes was significantly reduced. However, when production of a product which precipitated in 10% TCA was assessed following a second incubation at 37° C. for 30 minutes, it was noted that the LLMe resistant subset of lymphocytes produced almost no detectable amounts of this as yet unidentified product.

In experiment 2 (Table 8), PBL were divided into a CD4(+) T cell (T4 cell)-enriched population and a T8, NK-enriched population by staining with anti-CD4 or anti-CD8 monoclonal antibodies and panning on goat anti-mouse coated petri dishes to enrich for the unstained lymphocyte subsets as previously described (see prior Examples and J. Immunol. 1986 136:1038–1048). Again, it was noted that T4 cells took up less [³H]Leu-Leu-OMe during an initial incubation than did a population of lymphocytes enriched for T8 and NK cells. However, the differences in production of a product which precipitated in 10% TCA were even more dramatic. Whereas initial [³H]Leu-Leu-OMe uptake by T4 cells was approximately 53% of that seen with an equal number of T8 and NK cells, the amount of [³H]label appearing in a 10% TCA precipitate of the T4 cell sonicate after a subsequent 30 minute incubation was less than 7% of the quantity noted in the TCA precipitable of T8 and NK cell sonicates. Furthermore, little or no TCA insoluble product was produced by other non-lymphoid cell types such as dermal fibroblasts or a renal cell carcinoma line, Cur, which have been previously noted to be resistant to the toxicity of Leu-Leu-OMe (J. Immunol. 1986; 136:1038–1048). These findings, therefore, suggested an association between Leu-Leu-OMe toxicity and intracellular production of a presumably higher molecular weight product from [³H]Leu-Leu-OMe that was insoluble in 10% TCA. As proteinase K digestion removed this product, it was likely to be a larger peptide or protein into which [³H]Leu had been incorporated.

In additional experiments detailed in Table 9, it was noted that synthesis of this TCA precipitable material from Leu-Leu-OMe was not inhibited by a concentration of cycloheximide known to block ribosomal protein synthesis. This finding suggested that extraribosomal pathways of peptide or protein synthesis were likely to be involved in this process. A variety of proteases and peptidases have been noted to catalyze transpeptidation reactions when incubated with large concentrations of dipeptide esters (J. Biol. Chem. 1952; 195:645–656). When agents known to inhibit various forms of protease activity were aded during incubations of PBL with [³H]Leu-Leu-OMe, it was noted that the serine protease inhibitor, phenylmethylsulfonylfluoride (PMSF) did not inhibit generation of TCA insoluble material (Expt. 1, Table 9). Furthermore, levels of [³H]label in TCA precipitates actually increased when NH₄Cl was added at concentrations known to increase lysosomal pH and thereby inhibit the action of many lysosomal proteases (Expt. 2, Table 9). However, iodoacetamide almost completely inhibited synthesis of a TCA insoluble product of [³H]Leu-Leu-OMe (Expt. 1 and 2, Table 9). Iodoacetamide nonspecifically binds covalently to free sulfhydryl groups and thereby inhibits thiol protease function as well as other enzymatic reactions dependent on the presence of reduced sulfhydryl groups.

TABLE 9

PRODUCTION OF A TCA INSOLUBLE
PRODUCT FROM [³H]LEU—LEU—OME:
EFFECT OF VARIOUS INHIBITORS

| | | [³H]Leu—Leu—OMe Incorporation | |
|---|---|---|---|
| Expt. | Inhibitor (conc.) | Initial | 10% TCA Precipitate |
| | | | cpm |
| 1 | Nil | N.D. | 2,160 + 193 |
| | Cycloheximide, (100 micro-g/ml) | N.D. | 2,726 + 132 |
| | PMSF, 1 micro-M | N.D. | 2,078 + 213 |

TABLE 9-continued

PRODUCTION OF A TCA INSOLUBLE
PRODUCT FROM [$^3$H]LEU—LEU—OME:
EFFECT OF VARIOUS INHIBITORS

| Expt. | Inhibitor (conc.) | [$^3$H]Leu—Leu—OMe Incorporation | |
|---|---|---|---|
| | | Initial | 10% TCA Precipitate |
| | | cpm | |
| | Iodoacetamide (0.5 micro-M) | N.D. | 140 + 5 |
| 2 | Nil | 6,139 + 293 | 1,517 + 248 |
| | Iodoacetamide, (0.5 micro-M) | 6,316 + 188 | 243 + 16 |
| | NH$_4$Cl, (15 micro-M) | 5,746 + 1,272 | 3,275 + 261 |
| 3 | Nil | 8,751 + 106 | 1,015 + 145 |
| | Gly—Phe—CHN$_2$, (10$^{-6}$ M) | 8,691 + 522 | 104 + 55 |

Of note, however, glycylphenylalanine diazomethane (Gly-Phe-CHN$_2$), a selective and highly specific inhibitor of the thiol protease, dipeptidyl peptidase I (Cathepsin C) (J. Biol. Chem. 1981; 256:1923–1928) was similarly effective in blocking synthesis of a TCA insoluble product of [$^3$H] Leu-Leu-OMe. Dipeptidyl peptidase I has previously been noted to be present at high levels in the spleen of various meals (Proteinases in Mammalian Cells and Tissues, 1977; A. J. Barrett, ed., North-Holland Publishing Col, p. 314–322) and to be present in detectable levels in human peripheral blood (Biol. Soc. Trans. 1974; 2:432–434).

As detailed in Table 10, when lymphocyte subsets were highly purified by fluorescence activated cell sorting and then analyzed for dipeptidyl peptidase I activity, the levels of this enzyme within these cells was noted to vary greatly. Of special note, enzyme levels were highest in NK cells, monocytes (M-phi) and the cytotoxic T cell-enriched T8 cell subset. Furthermore, previously documented sensitivity to the toxic effects of Leu-Leu-OMe (second column, Table 10) was shown to be directly proportional to dipeptidyl peptidase I levels (third column, Table 10).

TABLE 10

CELLS WHICH ARE SENSITIVE TO THE TOXIC
EFFECTS OF LEU—LEU—OME HAVE A HIGH
CONTENT OF THE LYSOSOMAL THIOL PROTEASE,
DIPEPTIDYL PEPTIDASE I (CATHEPSIN C)

| Cell Type | Leu—Leu—OMe Sensitivity (LD$_{50}$) | Dipeptidyl Peptidase I (nMole-beta Naphthyl/hr/ micro-g protein)* |
|---|---|---|
| NK Cells | 35 micro-M | 2.54 |
| M-phi | 75 micro-M | 1.01 |
| T-8 Cells | 250 micro-M | 0.62 |
| B Cells | >500 micro-M | 0.13 |
| T4 Cells | >500 micro-M | 0.19 |
| Endothelial Cells | >500 micro-M | 0.14 |
| Renal Cell Carcinoma | >500 micro-M | 0.16 |

*The enzyme was assayed in cellular protein at 37° C. with 1 micro-M dithiothreitol with 200 micromolar glycyl L-phenylalamyl-beta napthylamide.

Dipeptidyl peptidase I is a lysosomal thiol peptidase which has been shown to remove amino terminal dipeptides from proteins. Alternatively, at neutral pH, incubation of this enzyme with high concentrations of dipeptide esters or amides has been shown to result in production of higher molecular weight polymerization products with the structure (R$_1$—R$_2$)$_n$—OR' (J. Biol. Chem. 1952; 195:645–656).

When R$_1$ and R$_2$ are amino acids with nonpolar side groups, such products are very hydrophobic and water insoluble (J. Biol. Chem. 1952; 195:645–656). As shown by the data displayed in Table 11, incubation of purified bovine dipeptidyl peptidase I (DPPI) at neutral pH with high concentrations of Leu-Leu-OMe results in production of a product which is insoluble in 10% TCA. Of note, much lower extracellular concentrations of Leu-Leu-OMe are required for production of a similar product within NK and T8 cells.

TABLE 11

LEU—LEU—OME IS METABOLIZED (POLYMERIZED)
TO A TCA INSOLUBLE PRODUCT BY DIPEPTIDYL
PEPTIDASE I (CATHEPSIN C)

| Concentration of Leu—Leu—OMe | Fractional Conversion of [$^3$H]Leu—Leu—OMe to a product which Precipitates in 10% TCA | |
|---|---|---|
| (micro-M) | Intact NK, T8 Cells | Purified DPPI |
| 1 | <0.1% | <0.01% |
| 10 | <0.2% | 0.03% |
| 100 | 11.1% | 0.08% |
| 250 | 23.2% | ND |
| 1000 | ND | 20.0% |

Since such cells appear to take up and concentrate this compound by a facilitated transport mechanism (FIGS. 10 and 11), it is likely that intracellular concentrations of Leu-Leu-OMe comparable to those required for polymerization of this compound by purified DPPI are achieved. These results, therefore, suggest that the 10% TCA insoluble product of Leu-Leu-OMe produced by cytotoxic lymphocytes can be accounted for by the actions of DPPI present within these cells.

Figure 12:
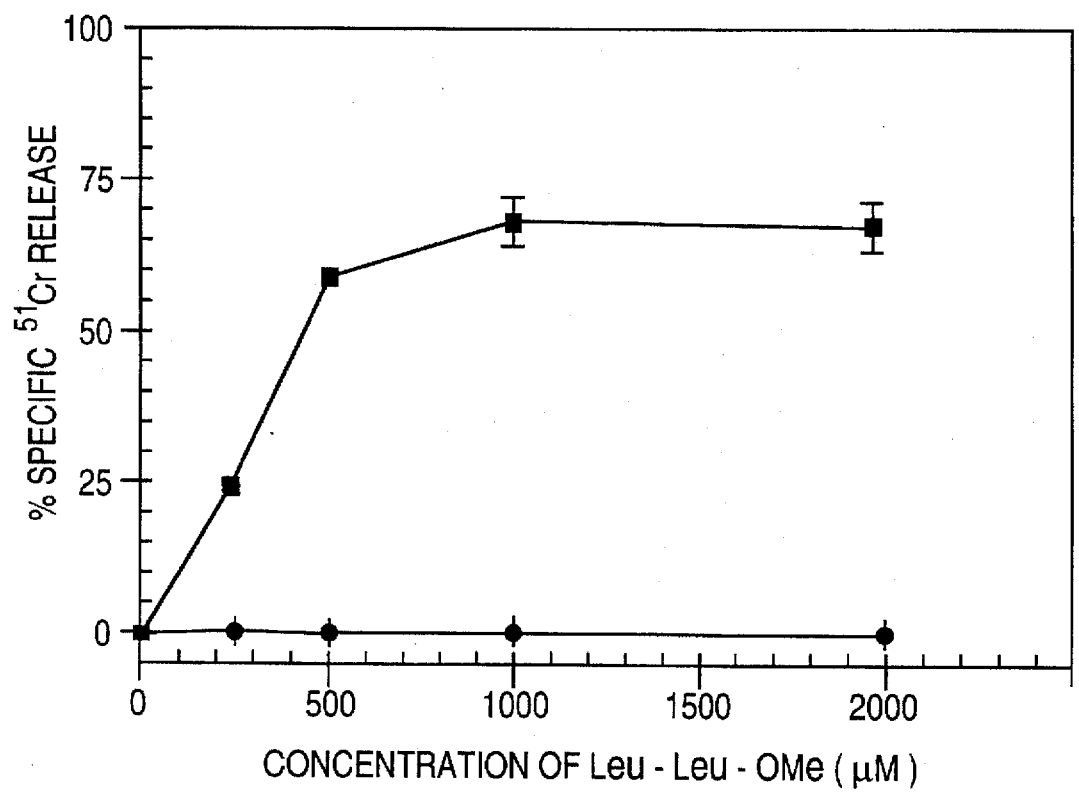
FIG. 12 schematically describes the effects upon RBC lysis by Leu-Leu-OMe in the presence (■) and absence (▲) of exogenous DPPI.

The following experiments were carried out to determine whether DPPI could generate a lytic product from Leu-Leu-OMe. In the experiment detailed in FIG. 12, $^{51}$Cr-labeled human erythrocytes (RBC) were incubated with varying concentrations of Leu-Leu-OMe alone (♦) or in the presence of purified bovine DPPI (■). As shown by the results displayed in FIG. 12, exposure of RBC to either DPPI or Leu-Leu-OMe alone results in no damage to RBC. However, in the presence of higher concentrations of Leu-Leu-OMe and DPPI, RBC lysis occurs. That such damage to erythrocyte cell membranes is likely to be related to production of a higher molecular weight hydrophobic polymer of Leu-Leu-OMe is demonstrated by the results of the experiment detailed in Table 12.

TABLE 12

RED BLOOD CELL LYSIS CAN BE MEDIATED BY
LEU-LEU-LEU-LEU-LEU-LEU-OME

| Compound Added | Concentration of Peptide Ester (micro-M) | $^{51}$Cr Release from RBC |
|---|---|---|
| Nil | 0 | 410 + 12 |
| LLOMe | 2500 | 482 + 121 |
| | 500 | 482 + 57 |
| | 100 | 400 + 27 |
| LLLLOMe | 500 | 457 + 41 |
| | 100 | 425 + 24 |
| LLLLLLOMe | 500 | 3,531 + 101 |
| | 100 | 6,129 + 400 |
| | 20 | 698 + 137 |

Table 12 shows results of an experiment, where $^{51}$Cr-labeled RBC's were incubated with varying concentrations of the methyl esters of the di-, tetra-, and hexa-peptides of leucine. Disruption of erythrocyte membranes was observed following exposure to the very hydrophobic compound (Leu)$_6$-OMe.

As detailed in Table 13, the specific inhibitor of DPPI, Gly-Phe-CHN$_2$ blocks the toxic effects of Leu-Leu-OMe.

TABLE 13

A SPECIFIC INHIBITOR OF DIPEPTIDYL PEPTIDASE I PREVENTS LEU—LEU—OME MEDIATED DEPLETION OF CD16(+) LYMPHOCYTES

| First Incubation | Second Incubation | Cells stained with | | |
|---|---|---|---|---|
| | | alpha-CD16 | alpha-CD4 | alpha-CD8 |
| Nil | Nil | 8.1 | 60.3 | 18.8 |
| Nil | Leu—Leu—OMe | <0.1 | 87.2 | 7.0 |
| Gly—Phe—CHN$_2$ | Nil | 8.4 | 64.0 | 21.6 |
| Gly—Phe—CHN$_2$ | Leu—Leu—OMe | 9.5 | 60.3 | 23.7 |

Thus, as previously reported (see prior Examples and J. Immunol. 1986; 136:1038–1048), exposure of human PBL to 250 micro-M Leu-Leu-OMe results in loss of all CD16(+) NK cells, and the majority of CD8(+) T cells and thereby results in reciprocal enrichment of the CD4(+) T cell subset which is largely Leu-Leu-OMe resistant (see Table 13). However, when preincubated with 10$^{-6}$M Gly-Phe-CHN$_2$, PBL were resistant to these effects of Leu-Leu-OMe and the fraction of viable CD16(+) and CD8(+) lymphocytes did not significantly change after Leu-Leu-OMe exposure.

Figure 13A:
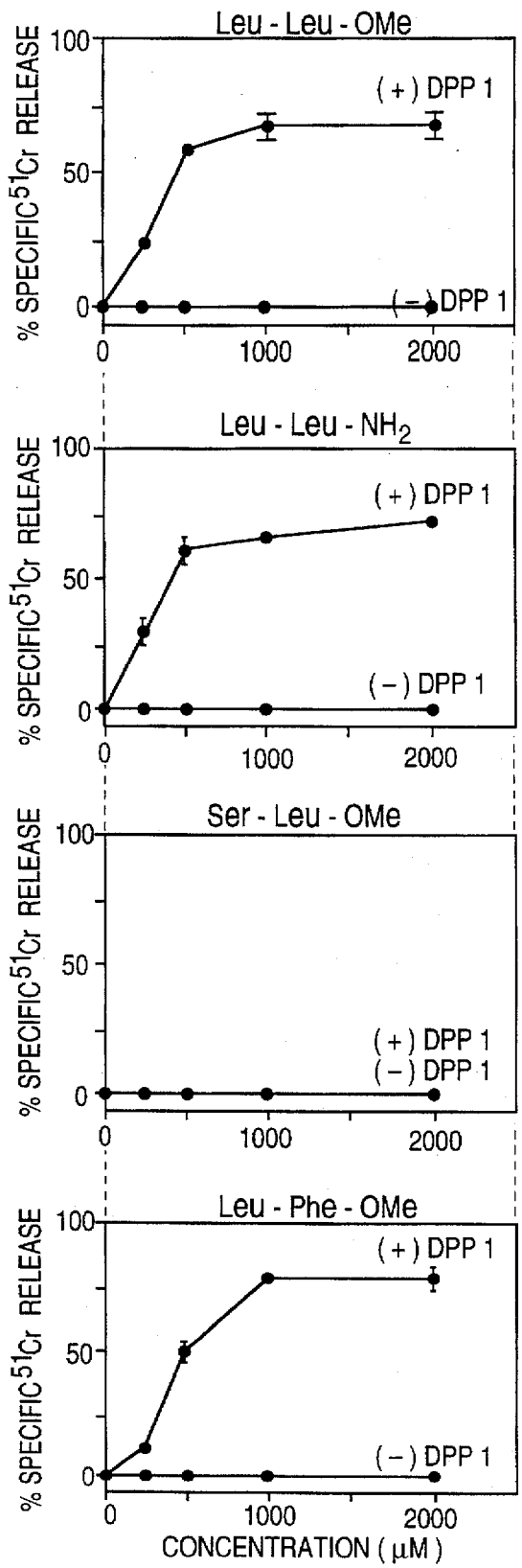
FIGS. 13A–13B show RBC lysis as dependent upon the presence (+) or absence (−) of DPPI with concentrations gradients of different dipeptide methyl esters.
Figure 13B:
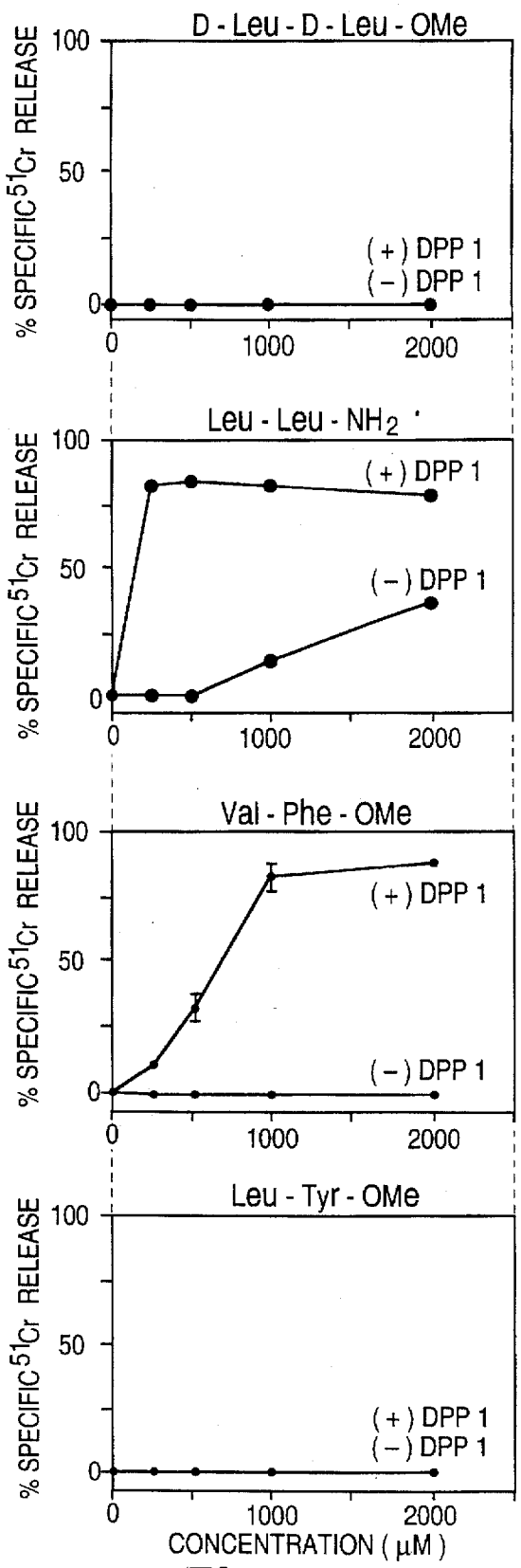

In the experiments detailed in FIG. 13, $^{51}$Cr-labeled RBC's were exposed to various dipeptide esters or amides in the presence ● or absence of purified DPPI. The results indicate that DPPI is unable to produce a membrane active metabolite from D-Leu-D-Leu-OMe or from dipeptide esters containing at least one amino acid with a polar side group such as serine or tyrosine. The first observation is probably related to the inability of this enzyme to catalyze transpeptidation of peptide esters containing D-stereoisomers of amino acids. The latter observations are likely to be related to the fact that polymers of Ser-Leu or Leu-Tyr are not hydrophobic and therefore unlikely to enter and disrupt cell membranes.

All of the compounds analyzed in FIG. 13 with the exception of Leu-Leu-NH$_2$ and Leu-Leu-OBenzyl have previously been assessed for NK toxicity (see prior examples and PNAS 1985; 82:2468–2472). In Table 14, results of experiments assessing the effects of these compounds on human NK function are detailed.

TABLE 14

INCUBATION OF MIXED LYMPHOCYTE POPULATIONS WITH LEUCYL-LEUCINE BENZYL ESTER RESULTS IN LOSS OF NK FUNCTION

| Addition During Preincubation | NK Function % Specific Lysis K562 |
|---|---|
| Nil | 66 |
| 12.50 micro-M Leu—Leu—OMe | 60 |
| 25.00 micro-M Leu—Leu—OMe | 12 |
| 50.00 micro-M Leu—Leu—OMe | 2 |
| 100.00 micro-M Leu—Leu—OMe | <1 |
| 6.25 micro-M Leu—Leu—OBenzyl | 62 |
| 12.50 micro-M Leu—Leu—OBenzyl | <1 |
| 25.00 micro-M Leu—Leu—OBenzyl | 1 |
| 250.00 micro-M Leu—Leu—NH$_2$ | 71 |
| 1.00 micro-M Leu—Leu—NH$_2$ | 66 |

These results indicate that whereas Leu-Leu-NH$_2$ exhibits no discernible toxicity for NK Cells, exposure to relatively low concentrations of Leu-Leu-OBenzyl ablates human NK activity. Indeed, Leu-Leu-OBenzyl is greater than twofold more potent than Leu-Leu-OMe with respect to the capacity to deplete human PBL of cytotoxic lymphocytes.

Table 15 contains a summary of data detailed in Tables 5, 6 and 14, FIG. 13, and in previous Examples (also PNAS 1985; 82:2468–2472; J. Immunol. 1986; 136:6038–1048) and of additional experiments which demonstrated that Leu-OMe and Leu-Leu are not polymerized by DPPI to form a product capable of lysing RBC's.

TABLE 15

FUNCTIONAL ACTIVITY OF VARIOUS AMINO ACID AND PEPTIDE DERIVATIVES

| Compound | Competitive Inhibition of $^3$H—Leu—Leu—OMe Uptake | Dipeptidyl Peptidase I Catalyzed Lysis of Human RBC | Toxicity NK Cells |
|---|---|---|---|
| Leu—Leu—OMe | +++ | +++ | +++ |
| Leu—OMe | – | – | – |
| Leu—Leu | ++ | – | – |
| Leu—Leu—NH$_2$ | – | +++ | – |
| Leu—Leu—OBenzyl | ++++ | +++++ | +++++ |
| Val—Phe—OMe | +++ | ++ | +++ |
| Leu—Phe—OMe | +++ | +++ | +++ |
| Leu—Tyr—OMe | ++++ | – | – |
| Ser—Leu—OMe | +++++ | – | – |
| D—Leu—D—Leu—OMe | – | – | – |

The data summarized in Table 15 indicate that all compounds mediating NK toxicity in assays performed in this and prior examples share two characteristics:

1. Such NK toxic reagents competitively inhibit [$^3$H]Leu-Leu-OMe uptake by human PBL and are therefore likely to be concentrated within lymphocytes by the same facilitated transport mechanism.

2. All NK toxic compounds are composed of amino acids with non-polar side groups and are suitable substrates for a DPPI catalyzed polymerization reaction which produces a hydrophobic product that disrupts erythrocyte cell membranes.

These studies, therefore, indicate that all dipeptide esters or amides with these characteristics (including Leu-Leu-OBenzyl, see Table 14) are likely to have the same immunosuppressive activities as the dipeptide alkyl esters reported earlier herein. Furthermore, these studies are the first to demonstrate that dipeptidyl peptidase I levels are selectively increased in cytotoxic lymphocytes. It can therefore be hypothesized that inhibition of this enzyme with Gly-Phe-CHN$_2$ or similar selective dipeptidyl peptidase I inhibitors should alter the function of these cells and therefore may act as an immunosuppressive agent of value in therapy of the same diseases or conditions as proposed for Leu-Leu-OMe or similar agents (albeit by a different mechanism).

EXAMPLE 14

NK Toxicity of Peptide Amides

These experiments were designed to assess the NK toxicity of dipeptide amides. In previous studies (see prior Examples and PNAS 82:2468–2472), the present inventors demonstrated that NK toxic effects of Leu-Leu-OMe were only seen when lymphocytes are exposed for 15 minutes at room temperature to Leu-Leu-OMe concentrations in excess of 12.5 micro-M. Whereas Leu-Leu-OBenzyl is a more potent NK toxin than is Leu-Leu-OMe, Leu-Leu-NH$_2$ has no demonstrable NK toxic effects (see Tables 14 and 15 of Example 13). The experiment detailed in Table 16 demonstrated that whereas Gly-Phe-OMe is a much less potent NK toxin than is Leu-Leu-OMe; and Gly-Phe-NH$_2$, like Leu-Leu-NH$_2$, has no apparent NK toxic effects; glycylphenylalanine-beta-naphthylamide is a very potent NK toxin.

TABLE 16

INCUBATION OF MIXED LYMPHOCYTE POPULATIONS WITH GLYCYL-PHENYLALANINE-BETA-NAPHTHYLAMIDE RESULTS IN LOSS OF NK FUNCTION

| Addition During Preincubation | NK Function % Specific Lysis K562 |
|---|---|
| Nil | 40.8 |
| 50 micro-M Leu—Leu—OMe | 1.1 |
| 250 micro-M Gly—Phe—OMe | 34.5 |
| 500 micro-M Gly—Phe—OMe | 10.1 |
| 250 micro-M Gly—Phe—NH$_2$ | 43.9 |
| 1 micro-M Gly—Phe—beta-Naphthylamide | 52.5 |
| 5 micro-M Gly—Phe—beta-Naphthylamide | 1.2 |
| 20 micro-M Gly—Phe—beta-Naphthylamide | 0.6 |

Additional studies demonstrated that Gly-Phe-beta-naphthylamide competitively inhibits [$^3$H]Leu-Leu-OMe uptake by lymphocytes, whereas simple amide derivatives of Leu-Leu-OMe do not compete for uptake by this facilitated transport mechanism.(see Table 15, Example 13).

On the basis of these findings and those contained in Table 14, Example 13, ester or amide derivatives of Leu-Leu or similar dipeptides which contain benzyl, naphthylamine or similar non-polar ring structures should prove to be selectively toxic for cytotoxic lymphocytes at lower concentrations than Leu-Leu-OMe and thus have enhanced clinical efficacy.

Figure 14A:
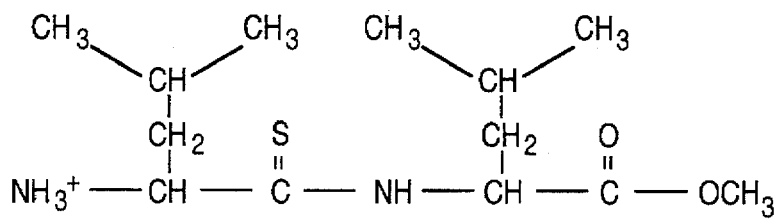
FIGS. 14A–14B show schematic structures of leucyl-(N) Methyl leucine methyl ester (B) and a thiopeptide analog of Leu-Leu-Ome (A).
Figure 14B:
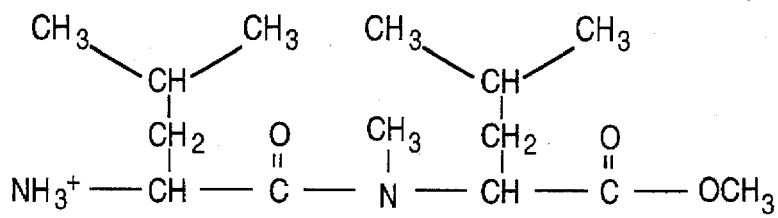

In addition, because the peptide bond between the first and second amino acid in Leu-Leu-OMe need not be cleaved in the mediation of NK toxicity, alterations of the peptide bond as detailed in FIG. 14, (i.e. a thiopeptide analog of Leu-Leu-OMe or the use of peptides such as leucyl-N-methyl leucine-methyl ester) may serve to produce an NK-toxic drug of equal or better concentration-dependent activity. As aminopeptidases capable of degrading Leu-Leu-OMe by cleavage of this peptide bond are less likely to degrade such compounds, they are more apt to have a longer in vivo half-life and therefore enhanced efficacy.

Figure 15A:
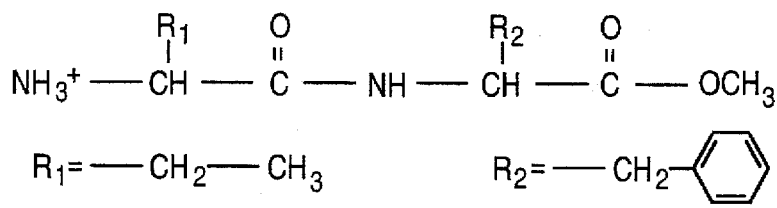
FIGS. 15A–15C show various examples of dipeptide esters with non-physiological R groups.
Figure 15B:
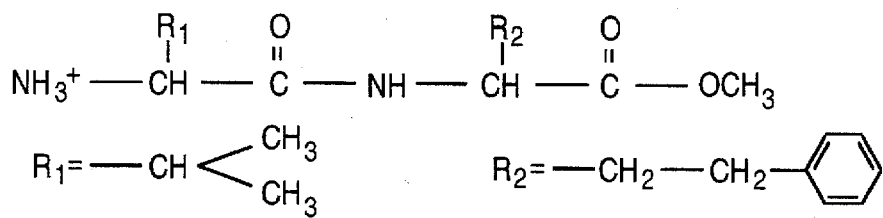
Figure 15C:
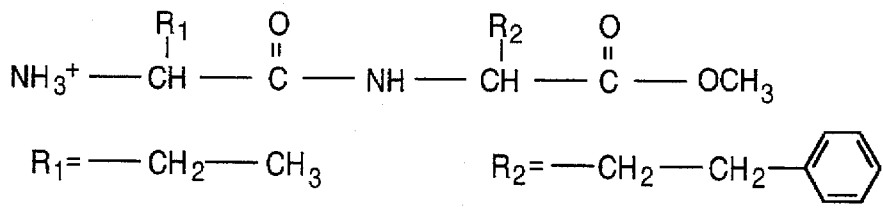

Modifications of amino acid R groups which preserve the non-polar nature of the amino acid R groups in dipeptide esters such as Leu-Leu-OMe and the activity of this compound as a substrate for dipeptidyl peptidase I should result in therapeutic agents with enhanced efficacy, since not all peptidases capable of degrading Leu-Leu-OMe may be able to degrade dipeptide esters containing non-physiologic side chains. Examples of some non-physiological dipeptide esters are detailed in FIG. 15, where, for simplicity, they are shown as dipeptide methyl esters only.

EXAMPLE 15

Prevention of Graft Versus Host Disease

Graft vs. host disease (GVHD) remains one of the major problems preventing an expanded use of human bone marrow transplantation (1,2). Although it is theoretically possible to avoid GVHD by careful histocompatibility matching, it is not currently feasible to match donor and recipient routinely for all major histocompatibility antigens. Moreover, there are no in vitro tests to detect minor antigenic disparities that can also stimulate GVHD (3). Because numerous studies in laboratory animals have shown that removal of immunocompetent T lymphocytes from the donor inoculum will prevent GVHD (4,5), the approaches to obviate GVHD in man have also focused on deleting T cells from the donor marrow. The available methodology for human T cell depletion, however, has not proven uniformly effective in preventing GVHD (6–9).

The present Example shows a new approach to the prevention of GVHD. Using a murine model of bone marrow transplantation, the effects of treating donor inoculum with L-leucyl-L-leucine methyl ester (Leu-Leu-OMe), a compound that eliminates cells with cytotoxic potential (10) was studied. Leu-Leu-OMe is toxic to human natural killer cells (NK), activated cytotoxic T cells (CTL), precursors of CTL (pre-CTL), and monocytes (see 11 and earlier Examples herein). Of importance, both CD8-positive and CD4-positive precursors and effectors of CTL are removed from mixed cell populations by Leu-Leu-OMe. By contrast, helper T cells, B cells, and a variety of nonhemopoietic cells are unaffected (see earlier Examples and 10, 11). Murine NK and pre-CTL were found to be very similar to human cells in concentration-dependent sensitivity to Leu-Leu-OMe (see earlier Examples and 12). To determine whether Leu-Leu-OMe might affect the induction of, or alter the pattern of tissue injury in GVHD, a murine model of bone marrow transplantation was used that is skewed toward GVHD in that it crosses major histocompatibility barriers and uses a severalfold excess of donor T cells. The experimental results predicted in earlier Examples and described here indicate that Leu-Leu-OMe treatment of the donor inoculum had the capacity to prevent lethal GVHD with no apparent toxic effects on stem cell function.

The methods used in this Example are described as follows:

Mice.

Female, 8–16-wk-old, C57BL/6J (B6) and (C57BL/6J x DBA/2J)F1 mice (B6D2F1) were used as donors and recipients, respectively. For some experiments B6 donors were immunized by injecting 70×10$^6$ cells/ml either in phosphate-buffered saline (PBS) or in Leu-Leu-OMe dissolved in PBS. Leu-Leu-OMe was synthesized from leucyl-leucine as previously described (10). After a 15 min incubation at room temperature, the cells were washed once, suspended in Hanks' balanced salt solution, counted, and infused via a lateral tail vein into irradiated (950 cGy) F1 recipients.

Immediately after treatment with Leu-Leu-OMe, there was less than a 5% loss of viable donor cells. Following a 3-h incubation at 37° C., however, the number of Lyt-2$^+$ spleen cells was decreased by more than 65%, whereas there was no alteration in the number of L3T4$^+$ cells (see earlier Examples and 12).

Survival studies.

Survival times were measured from the day of transplantation to the day of death. Deaths occurring within 8 d of transplantation were considered to be the result of radiation-induced gastroenteritis and were excluded. The nonparametric Mann-Whitney test was used to determine whether the median survival times (MST) differed between groups (14).

Assessment of spleen cell H-2 phenotype.

Spleen cells from control mice (normal B6 or B6D2F1) and long-term BMTx survivors (B6→B6D2F1) were depleted of B cells by panning on goat anti-mouse immunoglobulin-coated petri dishes (15). Aliquots of B cell-depleted spleen cells were incubated either with antibody 30-5-7.S (anti-L$^d$[16]), antibody 28-18-3.S (anti-k$^b$ [17]), or with a relevant isotype control antibody for 30 min at 4° C. Cells were then washed and incubated with a fluorescein isothiocyanate-labeled goat anti-mouse immunoglobulin (GAMIG-FITC, Cappell Laboratories, Cochranville, Pa.) and analyzed on a flow cytometer (Ortho system 50 HH, Ortho Diagnostics, Raritan, N.J.).

Measurement of stem cell function.

Bone marrow cells or marrow and spleen cell mixtures were incubated in PBS with or without 250 micro-M Leu-Leu-OMe as above and then infused into 950 cGy irradiated syngeneic recipients. 5 d later, splenic 5-iodo-2'-deoxyuridine-$^{125}$I ($^{125}$I-UdR) uptake was measured as previously described (15).

Histology.

Organs of recipient mice were fixed in 10% buffered formalin. Sections were stained with Hematoxylin and Eosin.

The results of this study are as follows:

Survival of transplanted mice.

Figure 16A:
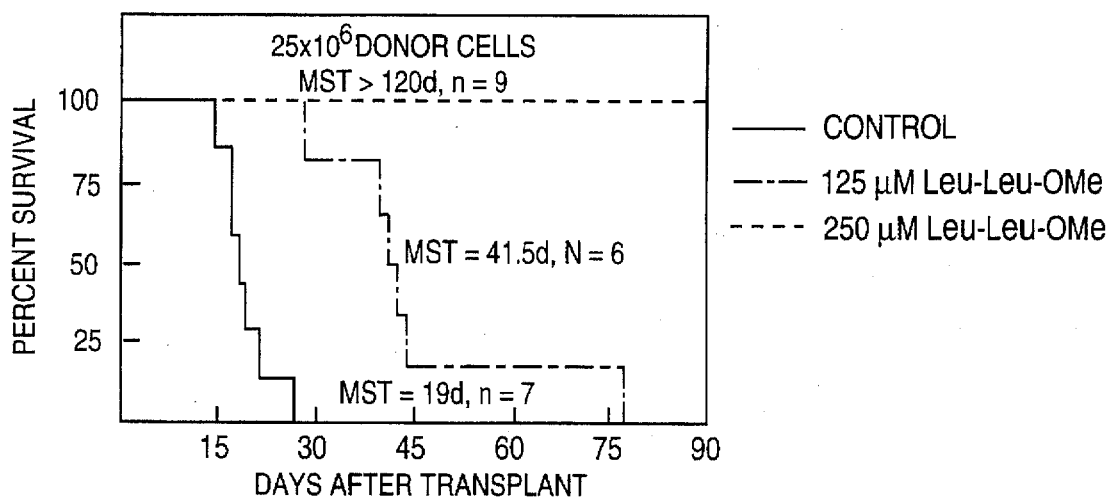
FIGS. 16A–B show the survival of naive B6→B6D2F1 mice. Donor bone marrow and spleen cells were obtained from naive B6 mice and mixed at various ratios prior to incubation and transfer into lethally irradiated B6D2F1 mice. (A) When $25 \times 10^6$ donor cells (spleen to marrow ratio 2.5:1) were transplanted, recipients of untreated cells had a median survival time (MST) of 19 d, recipients of cells treated with 125 micro-M Leu-Leu-OMe had a MST of 41.5 d (P<0.001), and recipients of cells treated with 250 micro-M Leu-Leu-OMe all survived >120 d. (B) When $50 \times 10^6$ donor cells (spleen to marrow ratio 5:1) were transplanted, recipients of untreated cells had an MST of 14 d, and recipients of cells treated with 250 micro-M Leu-Leu-OMe all survived >200 d.
Figure 16B:
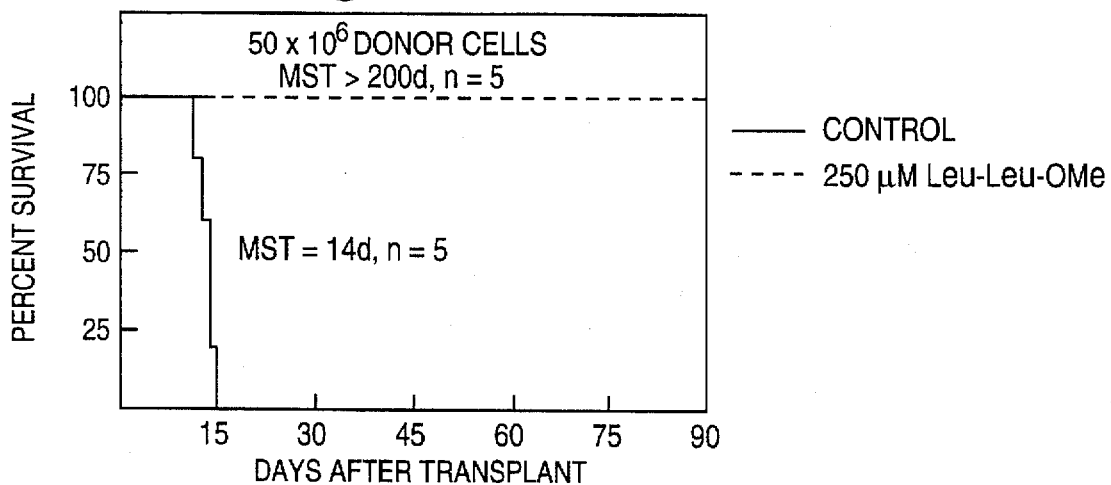

To assess the effects of Leu-Leu-OMe treatment of the donor inoculum on lethal GVHD, B6 donor cells were incubated with varying concentrations of Leu-Leu-OMe before infusing them into irradiated B6D2F1 recipients. As shown in FIG. 16, the recipients of $25 \times 10^6$ untreated donor cells died rapidly. Recipients given $25 \times 10^6$ cells preincubated with 125 micro-M Leu-Leu-OMe had significantly delayed mortality from GVHD (median survival time of 41.5 vs. 19 d, P<0.001), but all eventually died. By contrast, recipients of donor cells treated with 250 micro-M Leu-Leu-OMe all survived. Similar results were obtained in four separate experiments using $25 \times 10^6$ donor cells treated with 250 micro-M Leu-Leu-OMe. When the donor inoculum was doubled to $50 \times 10^6$ cells, all of the recipients of donor inocula treated with 250 micro-M Leu-Leu-OMe survived. Even when immune donors were used and the control mice experienced accelerated GVHD (FIG. 17), the recipients of donor cells treated with 250 micro-M Leu-Leu-OMe manifested significantly prolonged survival (median survival times of 49 vs. 11 d, P<0.001) and three of nine became long-term survivors.

GVHD-mediated tissue injury.

Control mice from all three experimental conditions exhibited acute cutaneous GVHD within 2 wk of transplantation, manifested clinically by alopecia and scaling, and histologically by epidermal basal layer liquefaction, epidermal lymphocytic infiltration, and a mononuclear cell infiltrate in the dermis. The recipients of $25 \times 10^6$ donor cells treated with 125 micro-M Leu-Leu-OMe also manifested evidence of acute GVHD, although at somewhat diminished intensity, whereas the recipients of $25 \times 10^6$ cells treated with 250 micro-M Leu-Leu-OMe had no evidence of cutaneous GVHD by inspection or biopsy early after transplantation and no evidence of GVHD in any target organs at the time of sacrifice, 125 d after bone marrow transplantation. By contrast, all five recipients of $50 \times 10^6$ Leu-Leu-OMe treated cells manifested acute cutaneous GVHD. Two of five developed a progressive widespread dermal sclerosis beginning 3 wk after transplantation. This was most severe 3 mo after transplantation and then substantially resolved. At the time of sacrifice (275 d after bone marrow transplantation) these two mice had only mild residual dermal sclerosis, and a mild to moderate periportal round cell infiltrate in the liver.

Demonstration of stable chimerism in mice transplanted with Leu-Leu-OMe treated cells.

To see whether the donor hemopoietic system remained dominant over that of the irradiated recipient, we characterized the H-2 phenotype of spleen cells from the mice used in the survival experiments at various times after transplantation. Spleen cells from normal B6 (donor, H-$2^b$) and B6D2F$_1$ (recipient, H-$2^b$/H-$2^d$) mice served as controls. Cells from three separate experimental groups analyzed as long as 275 d after transplantation consistently displayed the phenotype and staining pattern of the homozygous donor and not the H-2 heterozygous F1 recipient (>95% reactivity with anti-H-$2^b$, <1% reactivity with anti-H-$2^d$).

Lack of stem cell toxicity.

To assay the effects of Leu-Leu-OMe on hemopoietic stem cells, we incubated marrow or mixtures of marrow and spleen cells in PBS with or without Leu-Leu-OMe and measured splenic $^{125}$I-UdR uptake 5 d after transplantation into irradiated syngeneic recipients (18). Data in Table I indicate that treatment with 250 micro-M Leu-Leu-OMe had no deleterious effect on this measure of stem cell function. Since human marrow obtained for use in transplantation has variable amounts of peripheral blood contamination, we also studied the stem cell function of a mixture of murine spleen and marrow incubated with Leu-Leu-OMe. Again there was no decrement in $^{125}$I-UdR uptake, suggesting that "bystander" stem cells are not damaged when the numerous cytotoxic cells are lysed by Leu-Leu-Ome. Histologic examination of spleens 5 d after irradiation revealed the expected hypocellularity in the nontransplanted control group and equivalent erythrocytic, granulocytic, and megakaryocytic regeneration in the spleens of recipients of treated or nontreated marrow cells. Histological studies were conducted of spleens from irradiated mice. B6 mice were irradiated with 950 cGy and given no marrow (irradiation control), or given syngeneic bone marrow cells that had been incubated in PBS with or without 250 micro-M Leu-Leu-OMe. 5 d later spleens were examined histologically. Irradiation control spleens were sparsely populated, with no hemopoietic elements. Recipients of marrow treated with 250 micro-M Leu-Leu-OMe had the vast majority of their splenic red pulp packed with erythroblasts, but also had numerous peritrabecular areas containing megakaryocytes and granulocytic elements. A high power view of a recipient of marrow treated with 250 micro-M Leu-Leu-OMe (x200) and of a recipient of control marrow (x200) showed that the patterns of repopulation of these spleens were identical in megakaryocytes and granulocytes.

Figure 17:
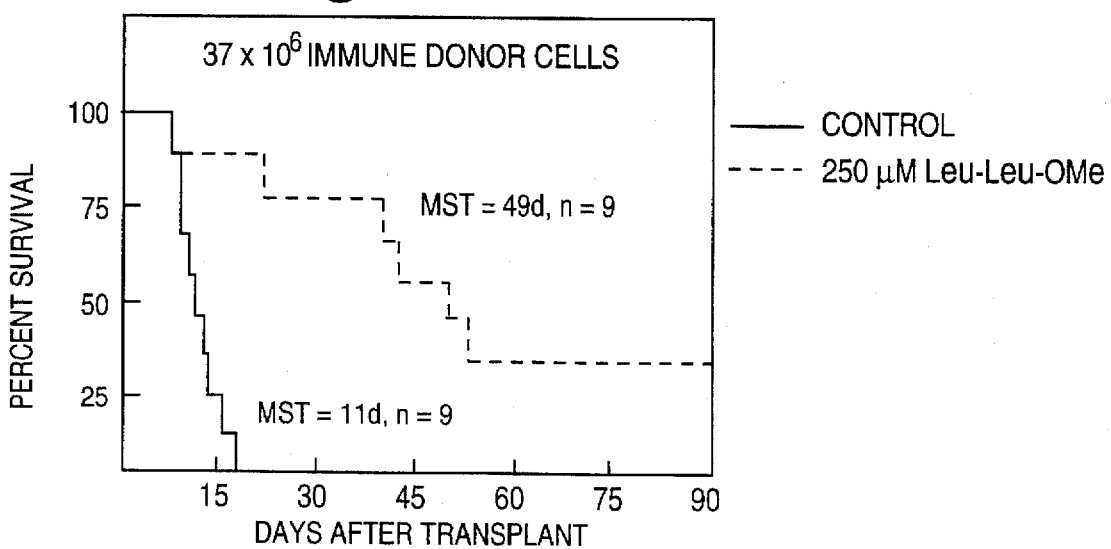
FIG. 17 shows the survival of immune B6→B6D2F1 mice. Donor bone marrow and spleen cells were obtained from B6 mice previously immunized against B6D2F1 alloantigens, incubated in the presence or absence of Leu-Leu-OMe, and then transferred into lethally irradiated B6D2F1 mice. When $37 \times 10^6$ donor cells (spleen to marrow ratio 3.7:1) were transplanted, recipients of untreated cells died with an MST of 11 d and recipients of cells treated with 250 micro-M Leu-Leu-OMe had a MST of 49 d (P<0.001). Three of nine of the mice receiving Leu-Leu-OMe treated cells survived >90 d.

This study indicates that Leu-Leu-OMe treatment of donor cells is able to prevent lethal GVHD across major histocompatibility barriers in this strain combination with no detectable stem cell toxicity. Since especially severe GVHD occurs when immune donors are used, it is noteworthy that one 15-min incubation of primed donor cells with 250 micro-M Leu-Leu-OMe nevertheless significantly increased survival (FIG. 17).

Spleen cells from surviving mice, assessed as long as 275 d after transplantation, consistently displayed the donor H-2 type, demonstrating that stable chimerism had been established. In addition, the absolute numbers of B cells, L3T4$^+$ and Lyt2$^+$ T cells, and NK function in the spleens of long-term B6→B6D2F1 chimeras were equivalent to that of age-matched animals transplanted with syngeneic bone marrow and spleen cells (B6→B6) (data not shown). Moreover, functional assessment of spleen cells from B6→B6D2F$_1$ chimeras indicated that the immune system of these animals had regained the capacity to proliferate and to generate cytotoxic T cells to third-party stimulators (H-$2^k$), but remained unresponsive to host alloantigens.

The mechanism whereby Leu-Leu-OMe prevents GVHD appears to be distinct from that of other regimens. The administration of anti-asialo $GM_1$ in vivo prevents lethal GVHD across minor histocompatibility barriers (19) but not across major-histocompatability barriers with the same dosage schedule. Using monoclonal antibodies to cell surface antigens, Korngold and Sprent (20) have recently shown that lethal GVHD resulting from a full H-2 mismatch can only be eliminated by removal of T cells with a pan-T cell reagent, and not with antibodies to either L3T4 or Lyt-2 alone. The incubation of human cells in vitro with 250 micro-M Leu-Leu-OMe selectively depletes those with cytotoxic potential regardless of phenotype (11); murine lymphocytes are similarly affected (12). Indeed, the Concentration-dependent capacity of Leu-Leu-OMe to eliminate murine splenic cytotoxic T cells closely parallels its efficacy in reducing the severity of GVHD. The incubation of B6 spleen cells with 100 micro-M Leu-Leu-OMe results in complete loss of NK function but only partial reduction of the generation of allospecific cytotoxic T cells (see prior Examples and 12). As predictable from the results above, incubation of B6 spleen and marrow cells with 125 micro-M Leu-Leu-OMe delayed, but did not eliminate death from GVHD (FIG. 16A). Treatment of cells with 250 micro-M Leu-Leu-OMe caused near total ablation of allocytotoxicity (12) and prevented lethal GVHD (FIGS. 16, A and B). The results support the hypothesis that the depletion of cytotoxic T cell precursors from the donor inoculum and the resultant absence of cytotoxicity during the interval between transplantation and hemopoietic reconstitution may have facilitated the development of stable chimerism in this strain combination. Alternatively, it may be that other unrecognized functions of these same Leu-Leu-OMe sensitive cells are important in the development of GVHD.

The histology of the long-term survivors revealed no evidence of GVHD in any target organ in recipients of 25 million treated cells 125 d after transplantation. The mild residual dermal sclerosis 275 d after transplantation in two of five mice receiving 50 million treated cells was not accompanied by epidermal, dermal, or follicular lymphocytic infiltration, and therefore appeared to be an inactive process. A periportal round cell infiltrate was observed in the livers of all five of these mice, however, suggesting that they developed a mild, nonscarring form of chronic hepatic GVHD. It appeared that the few cells with cytotoxic potential that remain after a single treatment with 250 micro-M Leu-Leu-OMe (<5%) (see prior Examples and 12) were insufficient in the $25 \times 10^6$ inoculum to cause any GVHD, but were sufficient in the $50 \times 10^6$ inoculum to cause the self-limited cutaneous GVHD and the mild chronic hepatic GVHD. However, the possibility remains that a Leu-Leu-OMe-resistant, noncytotoxic cell of low frequency in the donor inoculum caused the limited GVHD seen in the recipients of $50 \times 10^6$ B6 cells and the more severe GVHD seen in the recipients of immune B6 cells. Studies using other models of murine GVHD have suggested a role for helper T cells in causing a periportal lymphocytic infiltrate in the liver (21) and dermal sclerosis (22). These hypotheses are not mutually exclusive. It should be noted, however, that in the current studies even these nonlethal manifestations of GVHD were only observed when very large numbers of donor Leu-Leu-OMe treated donor cells were used.

The present studies clearly demonstrate the selective nature of the effects of Leu-Leu-OMe. Leu-Leu-OMe had no discernible toxicity for marrow stem cells, yet prevented GVHD. Erythroid regeneration, as assessed by splenic $^{125}$I-UdR uptake, was not diminished (Table 17) and newly generated granulocytic, erythrocytic and megakaryocytic elements were observed histologically following treatment with Leu-Leu-OMe. In contrast to current regimens used in human bone marrow transplantation, Leu-Leu-OMe treatment of donor marrow is a relatively rapid and simple technique. Because Leu-Leu-OMe appears to delete certain cells based on their functional capabilities, rather than on their cell surface markers, it may offer a new approach to avoid GVHD in humans.

TABLE 17

In Vivo Proliferation of Hemopoietic Stem Cells

| Experiment[1] | n[2] | Cells grafted | Treatment of cells | Splenic $^{125}$I-UdR uptake (96) geometric mean (95% CL)[3] |
|---|---|---|---|---|
| 1 | 8 | $3 \times 10^6$ | Vehicle | 0.87 (0.70–1.09) |
|   | 8 | $3 \times 10^6$ | Leu—Leu—OMe | 0.00 (0.78–1.28) |
|   | 5 | 0 |  | 0.01 |
| 2 | 11 | $3 \times 10^6$ | Vehicle | 0.48 (0.31–0.78) |
|   | 11 | $3 \times 10^6$ | Leu—Leu—OMe | 0.45 (0.30–0.67) |
|   | 6 | 0 |  | 0.01 |
| 3 | 6 | $3 \times 10^6$ | Vehicle | 2.72 (2.29–3.21) |
|   | 7 | $3 \times 10^6$ | Leu—Leu—OMe | 3.02 (2.32—3.91) |
| 4 | 8 | $4 \times 10^6$ | Vehicle | 1.06 (0.78–1.47) |
|   | 6 | $4 \times 10^6$ | Leu—Leu—OMe | 0.83 (0.46–1.50) |
| 5 | 6 | $2.5 \times 10^6$ | Vehicle | 1.28 (0.68–2.39) |
|   | 6 | $2.5 \times 10^6$ | Leu—Leu—OMe | 1.37 (1.10–1.46) |

[1]Marrow alone (experiments 1–3), or a mixture of spleen and marrow at a 4:1 ratio (experiments 4 and 5), were incubated either in PBS alone or in 250 micro-M Leu—Leu—OMe before being transferred into irradiated syngeneic recipients.
[2]Mice per group.
[3]CL, confidence limits).

References for Example 15

1. Gale, R. P. 1985. Graft-versus-host disease, *Immunol. Rev.* 88:193–214.
2. Storb, R., and E. D. Thomas. 1985. Graft-vs-host disease in dog and man: the Seattle Experience, *Immunol. Rev.* 88:215–238.
3. Tsoi, M. S., R. P. Warren, R. Storb, R. P. Witherspoon, E. Michelson, E. R. Giblett, M. S. Schanfield, P. Weiden, and E. Thomas. 1983. Autologous marrow recovery and sensitization to non-HLA antigens after HLA-identical marrow transplantation for aplastic anemia. *Exp. Hematol.* 11:73.
4. Korngold, R., and J. Sprent. 1978. Lethal graft-versus-host disease after one marrow transplantation across minor histocompatibility barriers in mice. *J. Exp. Med.* 148:1687–1698.
5. Vallera, D. A., C. C. B. Soderling, G. J. Carlson, and J. H. Kersey. 1981. Bone marrow transplantation across major histocompatibility barriers in mice. III. Treatment of donor grafts with monoclonal antibodies directed against Lyt determinants. *J. Immunol.* 128:871–875.
6. Hayward, A. R., S. Murphy, J. Githens, G. Troup, and D. Ambruso. 1982. Failure of a pan-reactive anti-T cell antibody, OKT 3, to prevent graft versus host disease in severe combined innnunodeficiency. *J. Pediatr.* 100:665–668.
7. Vogelsang, G. B., A.D. Hess, A. W. Berkman, P. J. Tutschka, E. R. Farmer, P. J. Converse, and G. W. Santos. 1985. An in vitro predictive test for graft versus host disease in patients with genotypic HLA-identical bone marrow transplants. *N. Engl. J. Med.* 313:645–650.
8. Beatty, P. G., R. A. Clift, E. M. Mickelson, B. B. Nisperos, N. Flournoy, P. J. Martin, J. E. Sanders, P. Stewart, C. D. Buckner, R. Storb, E. D. Thomas, and J. A. Hansen. 1985. Marrow transplantation from related donors other than HLA-identical siblings. *N. Engl. J. Med.* 313:765–771.

9. Goldman, J. M., J. F. Apperley, L. Jones, R. Marcus, A. W. G. Goolden, R. Batchelor, G. Hale, H. Waldmann, C. D. Reid, J. Hows, E. Gordon-Smith, D. Catovsky, and D. A. G. Galton. 1986. Bone marrow transplantation for patients with chronic myeloid leukemia. *N. Engl. J. Med.* 314:202–207.

10. Thiele, D. L., and P. E. Lipsky. 1985. Regulation of cellular function by products of lysosomal enzyme activity: elimination of human natural killer cells by a dipeptide methyl ester generated from L-Leucine methyl ester by monocytes or polymorphonuclear leukocytes. *Proc. Natl. Acad. Sci. USA.* 82:2468–2472.

11. Thiele, D. L., and P. E. Lipsky. 1986. The immunosuppressive activity of L-leucyl-L-leucine methyl ester: Selective ablation of cytotoxic lymphocytes and monocytes. *J. Immunol.* 136:1038–1048.

12. Thiele, D., M. Charley, J. Calomeni, and P. Lipsky. 1986. Selective depletion of cytotoxic cells with L-leucyl-L-leucine methyl ester prevents lethal graft-vs-host disease after transplantation of histo-incompatible bone marrow and spleen. *Clin. Res.* 34:673a. (Abstr.)

13. Charley, M. R., J. L. Bangert, B. L. Hamilton, J. N. Gilliam, and R. D. Sontheimer. Murine graft-versus-host skin disease: a chronological and quantitative analysis of two histologic patterns. *J. Invest. Dermatol.* 81:412–417.

14. Mann, H. B., and D. B. Whitney. 1947. On a test of whether one or two random variables is stochastically larger than the other. *Annals of Mathematics and Statistics.* 18:50–60.

15. Wysocki, L. J., and V. L. Sato. 1978. Panning for lymphocytes: A method for cell selection. *Proc. Natl. Acad. Sci. USA.* 75:2844.

16. Ozato, K., T. H. Hansen, and D. H. Sachs. 1980. Monoclonal antibodies to mouse MHC antigens. II. Antibodies to the H-2L$^d$ antigen, the products of a third polymorphic locus of the mouse major histocompatibility complex. *J. Immunol.* 125:2473.

17. Ozato, K., and D. A. Sachs. 1981. Monoclonal antibodies to mouse MHC antigens. III. Hybridoma antibodies reacting to antigens of the H-2$^d$ haplotype reveal genetic control of isotype expression. *J. Immunol.* 126:317.

18. Bennett, M., G. Cudkowicz, R. S. Foster, Jr., and D. Metcalf. 1986. Hemopoietic progenitor cells of W anemic mice studied in vivo and in vitro. *J. Cell. Physiol.* 71:211–226.

19. Charley, M. R., a. Mikhael, M. Bennett, J. N. Gilliam, and R. D. Sontheimer. 1983. Prevention of lethal minor-determinate, graft-versus-host disease in mice by the in vivo administration of anti-asialo GM$_1$. *J. Immunol.* 131:2101–2103.

20. Korngold, R., and J. Sprent. 1985. Surface markers of T cells causing lethal graft-vs-host disease to class I vs class II H-2 differences. *J. Immunol.* 135:3004–3010.

21. Van Rappard-Van Der Veen, Feikje M., T. Radaszkiewicz, L. Terraneo, and E. Gleichmann. 1983. Attempts at standardization of lupus-like graft-vs-host disease: inadvertent repopulation by DBA 2 spleen cells of H-2-different nonirradiated F1 mice. *J. Immunol.* 130:2693–2701.

22. DeClerk, Y., V. Draper, and R. Parkman. 1986. Clonal analysis of murine graft-vs-host disease. II. Leukokines that stimulate fibroblast proliferation and collagen synthesis in graft-vs. host disease. *J. Immunol.* 136:3549–3552.

The various published literature articles cited in this application are incorporated in pertinent part by reference herein for the reason cited.

Changes may be made in the construction, operation and arrangement of the various elements, steps and procedures described herein without departing from the concept and scope of the invention as defined in the following claims.

What is claimed is:

1. A method for deactivating natural killer cells or cytotoxic T-lymphocytes comprising treating said cells with an aqueous solution comprising a compound which competitively inhibits lymphocyte uptake of Leu—Leu—OMe and forms a membranolytic product, wherein said compound has the structure:

wherein

R1 and R2 represent hydrophobic side chains of amino acids;

X represents —OR3 or —NHR4;

R3 is selected from the group consisting of aryl, aralkyl, and alkyl; and

R4 is selected from the group consisting of alkyl, aryl, aralkyl and alkaryl.

2. The method of claim 1 wherein R3 is benzyl.

3. The method of claim 1 wherein said compound is Leu—Leu—O—CH$_2$—C$_6$H$_5$.

4. A method for inhibiting bone marrow graft-versus-host disease comprising the step of contacting bone marrow cells to be grafted with an aqueous solution comprising a compound which competitively inhibits lymphocyte uptake of Leu—Leu—OMe and forms a membranolytic product, wherein said compound has the structure:

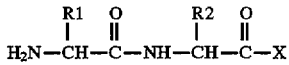

wherein

R1 and R2 represent hydrophobic side chains of amino acids;

X represents —OR3 or —NHR4;

R3 is selected from the group consisting of aryl, aralkyl, and alkaryl; and

R4 is selected from the group consisting of alkyl, aryl, aralkyl and alkaryl.

5. The method of claim 4 wherein R3 is benzyl.

6. The method of claim 4 wherein said compound is Leu—Leu—O—CH$_2$—C$_6$H$_5$.

* * * * *